(12) United States Patent
Volvovitz

(10) Patent No.: US 8,299,062 B2
(45) Date of Patent: Oct. 30, 2012

(54) PHARMACEUTICAL COMPOSITIONS AND METHODS FOR PREVENTING, TREATING, OR REVERSING NEURONAL DYSFUNCTION

(76) Inventor: Franklin Volvovitz, Woodbridge, CT (US)

( * ) Notice: Subject to any disclaimer, the term of this patent is extended or adjusted under 35 U.S.C. 154(b) by 1696 days.

(21) Appl. No.: 10/943,502

(22) Filed: Sep. 17, 2004

(65) Prior Publication Data

US 2009/0048234 A1 Feb. 19, 2009

Related U.S. Application Data

(60) Provisional application No. 60/504,361, filed on Sep. 18, 2003.

(51) Int. Cl.
*A61K 31/27* (2006.01)
*A61K 31/435* (2006.01)
*A61K 31/47* (2006.01)
*A61K 31/55* (2006.01)
*A61K 31/4353* (2006.01)
*A61K 31/4748* (2006.01)
*A61K 31/445* (2006.01)
*A61K 31/5513* (2006.01)
*A61K 31/551* (2006.01)
*A61K 31/216* (2006.01)

(52) U.S. Cl. ........ 514/215; 514/490; 514/295; 514/311; 514/297; 514/319; 514/304; 514/291; 514/317; 514/221; 514/220; 514/534

(58) Field of Classification Search .................. 514/215, 514/490, 295, 311, 297, 319, 304, 291, 317, 514/220, 221, 534
See application file for complete search history.

(56) References Cited

U.S. PATENT DOCUMENTS 5,760,049 A * 6/1998 Viner ............................. 514/291
6,369,052 B1 * 4/2002 Kellar et al. .................. 514/221

OTHER PUBLICATIONS

Lallement et al. Review of the Value of Huperzine as Pretreatment of Organophosphate Poisoning. Neurotoxicology 23, pp. 1-5 (May 2002).*
Raveh et al. Caramiphen and scopolamine prevent soman-induced brain damage and cognitive dysfunction. Neurotoxicology 23, pp. 7-17 (May 2002).*

* cited by examiner

*Primary Examiner* — Barbara P Badio
*Assistant Examiner* — Sara E Townsley
(74) *Attorney, Agent, or Firm* — Gary J. Gershik; Cooper & Dunham LLP

(57) ABSTRACT

The present invention provides compositions and methods for preventing, treating or reversing neuronal dysfunction in a mammal resulting from exposure to organophosphate nerve agents, organophosphate insecticides and incapacitating agents of the central nervous system (CNS); CNS injury, including traumatic brain injury, neurologic complications of cardiac surgery, perinatal asphyxia, and stroke, spinal cord injury, and peripheral nerve injury; and neuronal disorders associated with the loss of motor function including post-polio syndrome, amyotrophic lateral sclerosis, myasthenia gravis, Parkinson's disease and Rett syndrome; neurodegenerative disorders including Alzheimer's disease, mild cognitive impairment and schizophrenia; and cognitive impairment associated with aging. The compositions of the invention preferably comprise in effective amounts (a) at least one acetylcholinesterase inhibitor, (b) at least one compound with anticholinergic properties or both anticholinergic and anti-glutamatergic properties, (c) optionally an anticonvulsive compound, and a pharmaceutically acceptable carrier.

6 Claims, 1 Drawing Sheet

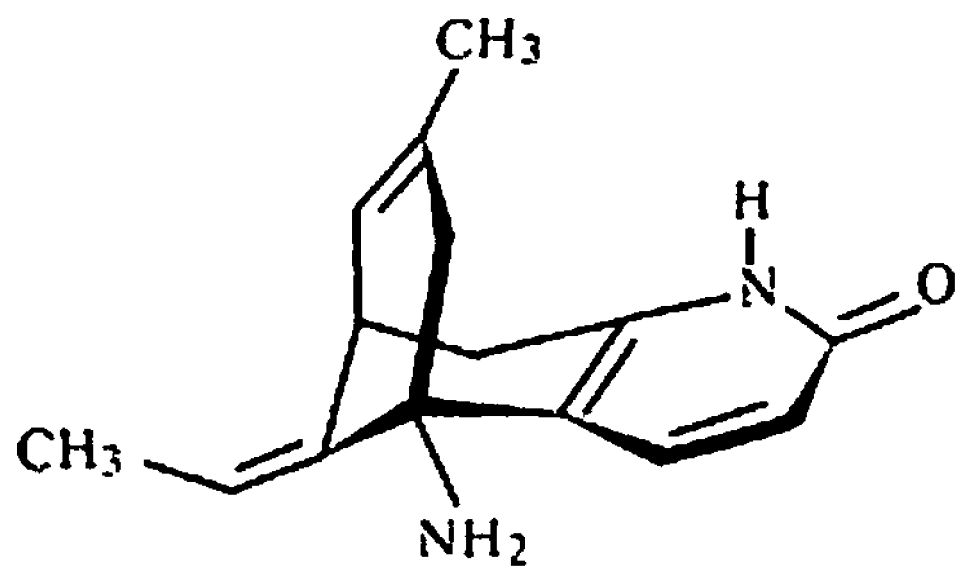
(-)-huperzine A

PHARMACEUTICAL COMPOSITIONS AND METHODS FOR PREVENTING, TREATING, OR REVERSING NEURONAL DYSFUNCTION

This application claims the benefit of U.S. Provisional Application No. 60/504,361, filed Sep. 18, 2003, hereby incorporated herein by reference in its entirety.

The present invention provides compositions and methods for preventing, treating or reversing neuronal dysfunction in an animal subject including humans resulting from exposure to organophosphate nerve agents, organophosphate insecticides and incapacitating agents of the central nervous system. The compositions and methods of the invention can also prevent, treat or reverse neuronal dysfunction in an animal subject including humans resulting from central nervous system injury, including without limitation traumatic brain injury, neurologic complications of cardiac surgery, perinatal asphyxia, and stroke, spinal cord injury, and peripheral nerve injury; and neuronal disorders associated with the loss of motor function including post-polio syndrome, amyotrophic lateral sclerosis, myasthenia gravis, Parkinson's disease and Rett syndrome; neurodegenerative disorders including Alzheimer's disease, mild cognitive impairment; and cognitive impairment associated with aging.

The compositions and methods of the invention can provide prophylactic or therapeutic neuroprotection in an animal subject including humans exposed to organophosphate nerve agents and organophosphate insecticides. The compositions and methods of the invention can also provide neuroprotection in cases of central nervous system injury including traumatic brain injury, neurologic complications of cardiac surgery, perinatal asphyxia, and stroke, spinal cord injury, and peripheral nerve injury; and neurodegenerative disorders including post-polio syndrome, amyotrophic lateral sclerosis, myasthenia gravis, Parkinson's disease, Rett syndrome, Alzheimer's disease, and mild cognitive impairment. The compositions and methods of the invention can also provide neuroprotection prophylactically in subjects with risk factors including age, genetics, family history for stroke or neurodegenerative disorders and in subjects prior to or in connection with medical procedures in which there is risk of neurologic injury including cardiac surgery.

The compositions of the invention preferably comprise (a) at least one acetylcholinesterase inhibitor or pharmaceutically acceptable salt or hydrate thereof, (b) at least one compound with anticholinergic properties or both anticholinergic and antiglutamatergic properties or pharmaceutically acceptable salt or hydrate thereof, and (c) optionally an anticonvulsive compound or pharmaceutically acceptable salt or hydrate thereof. The composition can further include a pharmaceutically acceptable vehicle, carrier, diluent, excipient, or delivery system and can be administered to an animal subject including a human, in connection with the methods of the invention to prevent, treat, or reverse neuronal dysfunction, or to provide prophylactic or therapeutic neuroprotection.

In one embodiment, the invention comprises a pharmaceutical composition wherein the active ingredients (a), (b) and optionally (c) above are present in amounts that render the composition effective in the prevention, treatment or reversal of neuronal dysfunction in a subject.

In a separate embodiment, the invention comprises a pharmaceutical composition wherein the active ingredients (a), (b) and optionally (c) above are present in amounts that render the composition effective in providing neuroprotection in a subject.

In another embodiment, the invention comprises a method of adjunctively administering to a subject an amount or amounts of (a), (b) and/or (c) above wherein such amounts render the combination of active ingredients effective in the prevention, treatment or reversal of neuronal dysfunction.

In another embodiment, the invention comprises a method of adjunctively administering to a subject an amount or amounts of (a), (b) and/or (c) above wherein such amounts render the combination of active ingredients effective in providing neuroprotection.

In still another embodiment, the invention comprises a method of providing neuroprotection, comprising contacting a neuron with (a), (b) and/or (c) in amounts effective to provide neuroprotection.

The acetylcholinesterase inhibitors are selected from:
huperzine compounds (HUP);
donepezil compounds (DNP);
tacrine compounds (THA);
rivastigmine (RVS);
galanthamine compounds (GLN)

The anticholinergic compounds are selected from:
atropine (ATR);
scopolamine (SCO)

The anticholinergic/antiglutamatergic compounds are selected from:
benactyzine (BNZ);
caramiphen (CRM);
trihexyphenidyl (THP)

The anticonvulsive compounds are selected from:
diazepam (DZP);
midazolam (MDZ)

Some of the above compounds are available from commercial sources. For example, (−)-huperzine, (±)-huperzine, tacrine, bis-7-tacrine, (−)-galanthamine, atropine, scopolamine, benactyzine, caramiphen, trihexyphenidyl, diazepam, and midazolam or their salts are available from Sigma-Aldrich Corporation, St Louis, Mo. (−)-Huperzine is commercially available as a dietary supplement ingredient and tacrine, (−)-galanthamine, donepezil, rivastigmine, atropine, scopolamine, benactyzine, caramiphen, trihexyphenidyl, diazepam, and midazolam or their salts are commercially available as prescription drugs. Additionally, methods for obtaining huperzine compounds, donepezil compounds, tacrine compounds, galanthamine compounds, salts, and hydrates thereof suitable for use in the compositions and methods of the invention are well known. For example, the various huperzine compounds, donepezil compounds, tacrine compounds, and galanthamine compounds can be synthesized according to the methods taught in the patents and publications listed in this application.

Among the acetylcholinesterase inhibitors huperzine compounds are especially preferred and among compounds with anticholinergic activity those with both anticholinergic and antiglutamatergic activity are especially preferred.

Attempts to use individual cholinesterase inhibitors, anticholinergic compounds, and antiglutamatergic compounds in the treatment of neurological diseases and disorders or to protect against nerve agent toxicity have at best achieved limited success and in many cases have not proven to be useful. Lack of clinical efficacy for a compound in a specific indication may be due to dose-limiting toxicities that prevent reaching the physiological concentrations needed for that compound to exert its therapeutic effect, disrupting normal physiological processes associated with therapeutic targets, and the existence of additional pathological mechanisms that are not affected therapeutically by a given compound.

There has been limited and variable success in protecting against organophosphate nerve agent toxicity in animals using either pyridostigmine bromide or physostigmine in combination with anticholinergic agents. Unfortunately, pyridostigmine bromide provides incomplete protection because it does not cross the blood brain barrier and the side effects of physostigmine limit its usefulness. Compounds that inhibit acetylcholinesterase may or may not also possess neuroprotective properties that may enhance protection. For example, by way of illustration but not limitation, although physostigmine, huperzine A, and donepezil are potent acetylcholinesterase inhibitors, laboratory studies have shown huperzine A and donepezil to have substantial neuroprotective properties, while physostigmine showed little or no neuroprotective action.

It is postulated that the present invention will provide qualitative and quantitative improvements in clinical benefits compared to those expected from the individual compounds alone or expected from pyridostigmine bromide or physostigmine based combinations. While not intending to be bound by any particular theory of operation, it is suggested that combinations of active ingredients in the present invention act synergistically upon multiple therapeutic targets as well as upon individual therapeutic targets at multiple sites making it possible to use dose levels that sufficiently favorably modulate pathological activity of a given therapeutic target to obtain clinical benefit without clinically disrupting its normal physiological function. One result of this may be to reduce the doses at which the individual compounds would otherwise be expected to provide a given therapeutic effect. By obtaining therapeutic efficacy at lower doses, it may be possible to reduce side effects thereby improving a compound's therapeutic index.

It is further postulated that the synergistic action of combinations of active ingredients in the present invention not only increases the therapeutic efficacy of the compounds compared to that displayed by the individual compounds alone, but also produces a novel therapeutic effect that would not otherwise be achievable by the individual compounds alone. In many neurological conditions parallel pathological mechanisms appear to contribute to neuronal dysfunction and injury. The potential therapeutic benefit derived from a single compound may be limited or masked as other pathological processes proceed unchecked. By acting broadly against these mechanisms, combinations of active ingredients may produce qualitatively superior results than could be achieved by any individual compound alone.

Additionally, the combinations of active ingredients in the present invention may reduce side effects that would otherwise be expected from individual compounds at a given dose thereby increasing the threshold dose for the onset of adverse reactions and allowing for the administration of compounds at higher dose levels. For example, without limitation, anticholinergic compounds may reduce specific cholinergic side effects of acetylcholinesterase inhibitors allowing said inhibitors to be safely used at higher doses. At the same time, acetylcholinesterase inhibitors may reduce the side effects of anticholinergic compounds allowing said compounds to be safely used at higher dose levels.

The commonly used names and systematic names of substances appearing herein are shown in Table 1.

TABLE 1

| Name of Substance | Source[1] | Systematic Name | Source[1] |
|---|---|---|---|
| atropine | NLM | Benzeneacetic acid, alpha-(hydroxymethyl)-, 8-methyl-8-azabicyclo(3.2.1)oct-3-yl ester, endo-(+−)- | USPDDN |
| atropine sulfate anhydrous | USPDDN | Benzeneacetic acid, alpha-(hydroxymethyl)-, 8-methyl-8-azabicyclo(3.2.1)oct-3-yl ester, endo-(+−)-, sulfate (2:1) (salt) | NLM |
| benactyzine | USPDDN | 2-Diethylaminoethyl benzilate | USPDDN |
| benactyzine hydrochloride | USPDDN | Benzilic acid, 2-(diethylamino)ethyl ester, hydrochloride | RTECS |
| caramiphen | USPDDN | Cyclopentanecarboxylic acid, 1-phenyl-, 2-(diethylamino)ethyl ester | RTECS |
| caramiphen hydrochloride | NLM | 2-Diethylaminoethyl 1-phenylcyclopentane-1-carboxylate hydrochloride | USPDDN |
| diazepam | NLM | 2H-1,4-Benzodiazepin-2-one, 7-chloro-1,3-dihydro-1-methyl-5-phenyl- | USPDDN |
| donepezil | NLM | 1H-Inden-1-one, 2,3-dihydro-5,6-dimethoxy-2-((1-(phenylmethyl)-4-piperidinyl)methyl)- | NLM |
| galanthamine | NLM | (4aS,6R,8aS)-4a,5,9,10,11,12-Hexahydro-3-methoxy-11-methyl-6H-benzofuro(3a,3,2-ef)(2)benzazepin-6-ol | USPDDN |
| huperzine A | NLM | 5,9-Methanocycloocta(b)pyridin-2(1H)-one, 5-amino-11-ethylidene-5,6,9,10-tetrahydro-7-methyl-, (5R,9R,11E)- | NLM |
| midazolam | USPDDN | 4H-Imidazo(1,5-a)(1,4)benzodiazepine, 8-chloro-6-(2-fluorophenyl)-1-methyl- | RTECS |
| rivastigmine | NLM | Carbamic acid, ethylmethyl-, 3-(1-(dimethylamino)ethyl)phenyl ester, (S)- | NLM |
| trihexyphenidyl | USPDDN | 1-Piperidinepropanol, alpha-cyclohexyl-alpha-phenyl- | RTECS |
| trihexyphenidyl | NLM | 1-Piperidinepropanol, alpha-cyclohexyl-alpha- | USPDDN |

[1]NLM: National Library of Medicine. USPDDN: United States Pharmacopoeia Dictionary of Drug Names. RTECS: Registry of Toxic Effects of Chemical Substances As used herein, the following terms shall have the following meanings.

As used herein, the phrase "huperzine compound" includes without limitation huperzine A, huperzine B; huperzine C, huperzine D and huperzinine (as described in "The alkaloids huperzines C and D and huperzinine from *Lycopodiastrum casuarinoides*. *Phytochemistry*, 37(6): 1759-1761, December 1994") and huperzine G (as described in "Structural Identification of Huperzine G. *Acta Botanica Sinica* 9(40):9, 1998"); analogs of huperzine A, huperzine B, huperzine C, huperzine D, huperzine G and huperzinine; derivatives of huperzine A huperzine B, huperzine C, huperzine D, huperzine G and huperzinine and salts and hydrates thereof. The term "huperzine compound" also encompasses all homologs, positional isomers, and all stereoisomers and mixtures of stereoisomers in optically active or racemic form of huperzine A, huperzine B, huperzine C, huperzine D, huperzine G and huperzinine and salts and hydrates thereof all of which for huperzine A and huperzine B are more fully depicted without limitation at column 5, lines 1-36 and column 7 line 21 to column 9 line 17 of U.S. Pat. No. 6,369,052 which patent is hereby incorporated herein by reference.

Examples of huperzine compounds include, but are not limited to, the huperzine analogs of structure IV depicted at column 2, lines 21-59 of U.S. Pat. No. 4,929,731; column 3, lines 1-39 of U.S. Pat. No. 5,106,979; column 2, lines 30-61 of U.S. Pat. No. 5,663,344; and column 2, lines 29-61 of U.S. Pat. No. 5,869,672; dihydro-desmethyl-huperzine, 11-desmethyl-11-chloro-huperzine A, and the compounds of structure I depicted at column 2, lines 8-62 of U.S. Pat. No. 5,104,880; the compounds of structures I, II, and III depicted at column 1, lines 15-51 of U.S. Pat. No. 5,177,082; the huperzine derivatives of structure II depicted at column 2, line 1 to column 4, line 6 of U.S. Pat. No. 5,929,084; and the huperzine analogs of structure I depicted at column 2, lines 18-40 of U.S. Pat. No. 5,547,960, all of which patents are hereby incorporated herein by reference.

Examples of huperzine compounds also include, but are not limited to dimeric compounds comprising huperzine fragments such as two 5-amino-5,6,7,8-tetrahydroquinoline monomers or similar moieties that may be the same or different of structures I and IA joined together by a divalent linking group depicted at column 2 line 57 to column 8 line 42 of U.S. Pat. No. 6,472,408 which patent is hereby incorporated herein by reference.

Preferred among these various huperzine compounds are huperzine A and huperzine B, including (−)-huperzine A, (+)-huperzine A, (±)-huperzine A, (−)-huperzine B, (+)-huperzine B, and (±)-huperzine B (as described in "The First Total Synthesis of (±) huperzine B. *Journal of Organic Chemistry.* 62(17):5978-5981, 1997 Aug. 22"), and the C-10 huperzine analogs described in U.S. Pat. No. 5,547,960 especially the (+), (−) and (±) forms of 10,10-dimethyl huperzine A and 10-methyl huperzine A. Also preferred among these various huperzine compounds are the huperzine fragment dimmers (HUPFD) described in U.S. Pat. No. 6,472,408 and depicted in Carlier et al., *Angew. Chem. Int. Ed.* 2000, 39(10), 1775-1777 especially N,N'-Di-5'-(5',6',7',8'-tetrahydroquinolin-2-onyl)-1,12-diaminododecane (HUPFD-12); N,N'-di-5'-(5',6',7',8'-tetrahydroquinolin-2-onyl)-1,13-diaminotridecane (HUPFD-13); and N,N'-di-5'-(5',6',7',8'-tetrahydroquinolin-2-onyl)-1,14-diaminotetradecane (HUPFD-14) including the (+), (−) and (±) forms and salts thereof.

As used herein the phrase "(−)-huperzine compound ((−)-HUP)" shall mean the subset of huperzine compounds that are (−) enantiomers; the phrase "(+)-huperzine compound ((+)-HUP)" shall mean the subset of huperzine compounds that are (+) enantiomers; and the phrase "(±)-huperzine compound ((±)-HUP)" shall mean the subset of huperzine compounds that are racemic mixtures of (−) enantiomers and (+) enantiomers.

(−)-Enantiomers and (+)-enantiomers of huperzine compounds can be separated from each other via chiral separation. For example, racemic (±)-10,10-dimethyl huperzine A (synthesized according to the method taught in Kozikowski et al., 1996, Bioorg. Med. Chem. Lett. 6:259) is resolved into its individual enantiomers by HPLC using a chiral column (e.g., CHIRALPAK AD Column, Daicel Chemical Industries, Ltd.) containing, for example, amylose tris (3,5-dimethylphenyl carbonate) coated on a 10 μm silica gel substrate and hexanes/ethanol/diethylamine (90/10/0.05) as the eluent. Samples can be prepared in ethanol (about 20 mg/ml) and then diluted with the mobile phase (about 2 ml) prior to injection. A flow rate of 4.0 ml/min. (at room temp.) on a semi-preparative column (25×1.0 cm) utilizing 300 μl per injection gives good results. The peaks can monitored using UV detection at 230 nm. The retention time is 10.3 min. for the (+)-isomer and 11.0 min. for the (−)-isomer. In addition to huperzine compounds, this method can be routinely adapted for isolating other optically active donepezil compounds, galanthamine compounds and tacrine compounds.

As used herein, the phrase "tacrine compound" includes without limitation tacrine, analogs of tacrine, derivatives of tacrine and salts and hydrates thereof. The term "tacrine compound" also encompasses all homologs, positional isomers and stereoisomers and salts and hydrates thereof. Examples of tacrine compounds also include, but are not limited to bifunctional compounds of structure I and particularly structure II depicted at column 1 line 49 to column 2 line 34 of U.S. Pat. No. 5,886,007 and of structure I and particularly structure II depicted at column 1 line 50 to column 2 line 32 of U.S. Pat. No. 5,783,584. Preferred among these bifunctional compounds are bis-tacrine analogs 1a-d depicted in FIG. 1 of U.S. Pat. No. 5,886,007 which patent is hereby incorporated herein by reference. Especially preferred is bis(7)-tacrine (1,7-N-heptylene-bis-9,9'-amino-1,2,3,4-tetrahydroacridine).

As used herein, the phrase "galanthamine compound" includes without limitation galanthamine, analogs of galanthamine, derivatives of galanthamine and salts and hydrates thereof. The term "galanthamine compound" also encompasses all homologs, positional isomers and stereoisomers and salts and hydrates thereof. Preferred among these are (−)-galanthamine,(+)-galanthamine, and (±)-galanthamine. The isolation of galanthamine of galanthamine by extraction from plants is described in U.S. Pat. No. 6,573,376, methods of producing galanthamine analogs are described in U.S. Pat. No. 6,569,848 and methods of synthesizing (−)-galanthamine are described in U.S. Pat. No. 6,392,038, additional methods for synthesizing (±)-galanthamine and (−)-galanthamine compounds are described in U.S. Pat. No. 5,428,159 which patents are hereby incorporated herein by reference.

As used herein, the phrase "donepezil compound" includes without limitation donepezil, analogs of donepezil, derivatives of donepezil and salts and hydrates thereof. The term "donepezil compound" also encompasses all homologs, positional isomers and stereoisomers and salts and hydrates thereof. Preferred among these are (−)-donepezil, (+)-donepezil, and (±)-donepezil. The synthesis of donepezil and its analogs are described in U.S. Pat. Nos. 6,492,522, 6,252,081, 6,245,911, 6,140,321 and 5,985,864 which patents are hereby incorporated herein by reference.

The phrase "compounds of the invention" includes huperzine compounds, donepezil compounds, tacrine compounds, rivastigmine, galanthamine compounds, atropine, scopolamine, benactyzine, caramiphen, trihexyphenidyl, diazepam, and midazolam and pharmaceutically acceptable salts thereof or hydrates thereof.

The phrase "composition of the invention" means a composition comprising (a) at least one acetylcholinesterase inhibitor selected from among huperzine compounds (HUP), donepezil compounds (DNP), tacrine compounds (THA), rivastigmine (RVS), and galanthamine compounds (GLN), pharmaceutically acceptable salts thereof or hydrates thereof; (b) at least one compound with anticholinergic properties selected from among atropine (ATR) and scopolamine (SCO) or both anticholinergic and antiglutamatergic properties selected from among benactyzine (BNZ), caramiphen (CRM), and trihexyphenidyl (THP), pharmaceutically acceptable salts thereof or hydrates thereof and (c) optionally an anticonvulsive compound selected from among diazepam (DZP) and midazolam (MDZ) or pharmaceutically acceptable salt or hydrate thereof. Preferably, compositions of the invention are pharmaceutical compositions comprising (a) at least one acetylcholinesterase inhibitor selected from among huperzine compounds (HUP), donepezil compounds (DNP), tacrine compounds (THA), rivastigmine (RVS), and galanthamine compounds (GLN), pharmaceutically acceptable salts thereof or hydrates thereof; (b) at least one compound with anticholinergic properties selected from among atropine (ATR) and scopolamine (SCO) or both anticholinergic and antiglutamatergic properties selected from among benactyzine (BNZ), caramiphen (CRM), trihexyphenidyl (THP), pharmaceutically acceptable salts thereof or hydrates thereof and (c) optionally an anticonvulsive compound selected from among diazepam (DZP) and midazolam (MDZ) or pharmaceutically acceptable salts or hydrates thereof, in amounts effective in providing neuroprotection to a subject or effective in preventing, treating or reversing neuronal dysfunction in a subject, and a pharmaceutically acceptable vehicle, carrier, or delivery system. A pharmaceutically acceptable vehicle or carrier can comprise a carrier, excipient, diluent, or a mixture thereof.

The phrase "adjunctively administering" means administering (a), (b) and/or (c) to a subject in a sequence and within a time interval such that they can act together to provide neuroprotection or to treat, prevent, or reverse neuronal dysfunction. For example, the compounds of the invention can be administered simultaneously in the same or separate compositions. When administered in separate compositions, a different administration mode can be used for each composition.

The phrase "pharmaceutically acceptable salt(s)," as used herein includes, but is not limited to, salts of acidic or basic groups that may be present in the huperzine compounds, donepezil compounds, tacrine compounds, rivastigmine, galanthamine compounds, atropine, scopolamine, benactyzine, caramiphen, trihexyphenidyl, diazepam, and midazolam and hydrates thereof. Huperzine compounds, donepezil compounds, tacrine compounds, rivastigmine, galanthamine compounds, atropine, scopolamine, benactyzine, caramiphen, trihexyphenidyl, diazepam, midazolam, and hydrates thereof that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, edetate, camsylate, carbonate, bromide, chloride, iodide, citrate, dihydrochloride, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate (i.e., 1,1'-methylene-bis-(2-hydroxy-3-naphthoate)). Huperzine compounds, donepezil compounds, tacrine compounds, rivastigmine, galanthamine compounds, atropine, scopolamine, benactyzine, caramiphen, trihexyphenidyl, diazepam, midazolam, and hydrates thereof that include an amino moiety can also form pharmaceutically acceptable salts with various amino acids, in addition to the acids mentioned above. Huperzine compounds, donepezil compounds, tacrine compounds, rivastigmine, galanthamine compounds, atropine, scopolamine, benactyzine, caramiphen, trihexyphenidyl, diazepam, midazolam, and hydrates thereof that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, the term "hydrate" means huperzine compounds, donepezil compounds, tacrine compounds, rivastigmine, galanthamine compounds, atropine, scopolamine, benactyzine, caramiphen, trihexyphenidyl, diazepam, midazolam, or a pharmaceutically acceptable salt thereof that further includes a stoichiometric or non-stoichiometric amount of water bound to it by non-covalent intermolecular forces.

In one embodiment, "treatment" or "treating" refers to an amelioration, prophylaxis, or reversal of a disease or disorder, or at least one discernible symptom thereof. In another embodiment, "treatment" or "treating" refers to an amelioration, prophylaxis, or reversal of at least one measurable physical parameter, not necessarily discernible in or by the subject. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder, for example, by inhibiting underlying pathological processes before they reach clinical significance.

In certain embodiments, the compounds of the invention are administered as a preventative measure. As used herein, "prevention" or "preventing" refers to a reduction of the risk of acquiring a given disease or disorder. In a preferred mode of the embodiment, the compounds of the invention are administered as a preventative measure to a subject at risk of exposure to organophosphate nerve agents or insecticides, to a subject prior to cardiac surgery, to a subject at risk of stroke, to a subject at risk of post-polio syndrome or having a genetic or non-genetic predisposition to neuronal dysfunction, such as Alzheimer's disease, Rett syndrome or cognitive impairment even though symptoms of the disorder are absent or minimal.

The term "neuroprotection" as used herein, means preventing, treating, or reversing the loss of neurons, injury to neurons or the loss of neuronal function including without limitation such losses and injury associated with exposure to organophosphate nerve agents or insecticides, medical procedures such as cardiac surgery, central nervous system injuries such as perinatal hypoxia, traumatic brain injury and stroke, and neurodegenerative disorders such as a Alzheimer's disease, amyotrophic lateral sclerosis, Rett syndrome, post-polio syndrome, and Parkinson's disease.

"Disease" refers to any deviation from or interruption of the normal structure or function of any part, organ, or system (or combination thereof) of the body that is manifested by a characteristic set of symptoms and signs and whose etiology, pathology, and prognosis may be known or unknown. Dorland's Illustrated Medical Dictionary, W. B. Saunders Co., 27th ed. (1988).

"Disorder" refers to any derangement or abnormality of function; a morbid physical or mental state. Dorland's Illustrated Medical Dictionary, W. B. Saunders Co., 27th ed. (1988).

The term "subject" refers to any animal, preferably a mammal, to which will or has been administered compounds or compositions of the invention to provide a neuroprotective effect or to prevent, treat or reverse neuronal dysfunction. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of neuroprotection or in need of prevention, treatment or reversal of neuronal dysfunction.

Formulation and Routes of Administration

The compounds of the invention can be administered according to the methods of the invention by virtually any mode including, but not limited to, oral, nasal, parenteral, transdermal, and buccal administration, etc. The compounds of the invention can be administered adjunctively, for example, simultaneously or serially in either order. When administered serially, the compounds of the invention should be administered sufficiently close in time so as to provide the desired effect. For initial administration, serially administered compounds should be administered within 1-2 hours, preferably 1 hour, and more preferably within 0.5 hour of each other. Depending on the half-life, formulation and route of administration, a compound may be re-administered one or more times without re-administering the other compounds to main optimal therapeutic effectiveness over a period of time.

The compounds can be adjunctively administered therapeutically to treat, prevent, reverse, or slow the rate of onset of neuronal dysfunctions, such as cognitive decline, memory impairment, muscle weakness or CNS injury, or prophylactically to either protect against further neuronal dysfunction associated with these processes or to avoid or forestall the onset of neuronal dysfunction altogether. For example, the compositions of the invention can be adjunctively administered prophylactically to healthy subjects to slow or halt the progression of age-associated declines in memory or cognition or, depending upon the age of the subject, to avoid age-associated declines in memory or cognition altogether. In some instances, the treatment can even enhance or improve cognitive function, particularly memory acquisition, storage or retrieval or concentration (focus) or the performance of complex tasks.

The compounds of the invention can be adjunctively administered to a subject, including a human, using a wide variety of routes or modes of administration. Suitable routes of administration include, but are not limited to, oral inhalation; nasal inhalation; transdermal; oral; rectal; transmucosal; intestinal; and parenteral administration, including intramuscular, subcutaneous, and intravenous injections. The compounds of the invention can be administered via the same or via a different mode of administration. For example, a huperzine compound, pharmaceutically acceptable salt or hydrate can be administered transdermally and caramiphen, pharmaceutically acceptable salt or hydrate can be administered orally. Additionally, the same compound or class of compound can be administered by two different routes. Various combinations of compounds of the invention can be administered. In addition, the compounds of the invention can be administered in cocktails combined with other therapeutic agents. Of course, the choice of therapeutic agents that can be co-administered with the composition of the invention will depend, in part, on the condition being treated. For example, the compounds of the invention can be administered in cocktails comprising other agents used to treat the pain and other symptoms and side effects commonly associated with neuronal dysfunction, such as cognitive decline and CNS injury. The compounds of the invention can also be administered in cocktails containing other agents that are commonly used to treat the above conditions.

The compounds of the invention can be formulated either as single compounds per se or as mixtures of compounds of the same type (e.g., two different huperzine compounds), or they can be formulated together in the form of a composition. Such compositions will generally comprise (a) at least one acetylcholinesterase inhibitor selected from among huperzine compounds (HUP), donepezil compounds (DNP), tacrine compounds (THA), rivastigmine (RVS), and galanthamine compounds (GLN), pharmaceutically acceptable salts thereof or hydrates thereof; (b) at least one compound with anticholinergic properties selected from among atropine (ATR) and scopolamine (SCO) or both anticholinergic and antiglutamatergic properties selected from among benactyzine (BNZ), caramiphen (CRM), and trihexyphenidyl (THP), pharmaceutically acceptable salt thereof or hydrate thereof and (c) optionally an anticonvulsive compound selected from among diazepam (DZP) and midazolam (MDZ) or pharmaceutically acceptable salt or hydrate thereof. The formulations will generally include (a), (b) and optionally (c) and one or more pharmaceutically acceptable carriers, excipients or diluents. Pharmaceutical compositions for use in accordance with the present invention can be formulated in conventional manner using one or more physiologically acceptable carriers, excipients, diluents or auxiliaries that facilitate processing of the compounds of the invention into compositions of the invention that can be used pharmaceutically. The choice of formulation is dependent upon the selected administration route.

For oral administration, the compounds of the invention can be formulated with pharmaceutically acceptable carriers well known in the art. Such carriers enable the compounds of the invention to be formulated for oral administration as tablets, pills, gums dragées, capsules, liquids, gels, syrups, slurries, suspensions and the like. Alternatively, the compounds can be formulated into candies, cookies, or other edible foodstuffs. Pharmaceutical preparations for oral use can be obtained by mixing the compounds of the invention with a solid excipient, optionally grinding the resulting mixture, and processing the mixture of granules, after adding suitable auxiliaries, if desired, to obtain tablets or dragée cores. Suitable excipients include, but are not limited to, fillers, such as sugars, including lactose, sucrose, mannitol, or sorbitol; cellulose preparations, such as maize starch, wheat starch, rice starch, potato starch, gelatin, gum tragacanth, methylcellulose, hydroxypropylmethyl-cellulose, sodium carboxymethylcellulose, and polyvinylpyrrolidone (PVP). If desired, disintegrating agents can be added, such as cross-linked polyvinyl pyrrolidone, agar, or alginic acid or a salt thereof, such as sodium alginate.

Particularly preferred oral formulations are fast dispersing solid dosage forms that preferably dissolve in the oral cavity within sixty (60) seconds, more preferably within thirty (30) seconds, most preferably within ten (10) seconds as described in U.S. Pat. No. 6,509,040 which patent is hereby incorporated herein by reference. Also preferred are rapidly dissolving dosage forms that dissolve in the oral cavity within about 90 seconds or less and that can contain both rapid release and or sustained release particles as described in U.S. Pat. No. 6,221,392 which patent is hereby incorporated herein by reference.

Also preferred are oral formulations in which one or more of the compounds of the invention is individually formulated for a sustained delivery profile to optimize the therapeutic effectiveness of the combination of such compounds in the composition of the invention. Such sustained delivery profiles take in to account the preference to sustain within target ranges blood and tissue levels of compounds that may have different half-lives and different adsorption profiles. Without limitation, one such formulation providing for both controlled release of compound and a rapidly dissolving dosage form is described in U.S. Pat. No. 6,413,549 which patent is hereby incorporated herein by reference.

In one embodiment, the compounds of the invention are formulated, either singly or together in long acting formulations can be administered by implantation or transcutaneous delivery (for example subcutaneously or intramuscularly), intramuscular injection, or transdermally. Thus, for example, the compounds of the invention can be formulated with suitable polymeric or hydrophobic materials (such as an emulsion in an acceptable oil) or ion exchange resins, or as sparingly soluble derivatives, for example, as a sparingly soluble salt.

Preferred depot preparations are those that are suitable for transdermal administration, such as a transdermal patch. As the compounds of the invention, pharmaceutically acceptable salts or hydrates are readily absorbed and cross cell membranes and the blood-brain barrier they can be incorporated into patches and formulations for transdermal delivery. Patches and formulations adaptable for transdermal administration of compounds of the invention are described in U.S. Pat. Nos. 5,725,876; 5,716,635; 5,633,008; 5,603,947; 5,411,739; 5,364,630; 5,230,896; 5,004,610; 4,943,435; 4,908,213; and 4,839,174, which patents are hereby incorporated herein by reference. Preferably, the compounds of the invention are formulated into a single transdermal patch.

For injection, the compounds of the invention can be formulated in physiologically compatible aqueous solutions, such as Hanks's solution, Ringer's solution, or physiological saline buffer. For transmucosal administration, penetrants appropriate to the barrier to be permeated are used in the formulation. Such penetrants are generally known in the art.

Dragée cores are provided with suitable coatings. For this purpose, concentrated sugar solutions can be used that can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or dragée coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the compounds of the invention in an admixture with filler, such as lactose; binders, such as starches; or lubricants, such as talc or magnesium stearate; or stabilizers. In soft capsules, the compounds of the invention can be dissolved or suspended in suitable liquids, such as fatty oils, liquid paraffin, or liquid polyethylene glycols. In addition, stabilizers can be added to the soft-capsule formulation. All formulations for oral administration should be in dosages suitable for such administration.

For buccal administration, the compositions can take the form of oral sprays, tablets, gums, or lozenges formulated by well-known methods.

A candy formulation suitable for oral or buccal administration that can be adapted to the compounds of the invention is described in U.S. Pat. No. 6,083,962, which is hereby incorporated herein by reference. Additional formulations suitable for oral or buccal administration of the compounds of the invention are described in U.S. Pat. Nos. 5,939,100; 5,799,633; 5,662,920; 5,603,947; 5,549,906; D358,683; U.S. Pat. Nos. 5,326,563; 5,293,883; 5,147,654; 5,035,252; 4,967,773; 4,907,606; 4,848,376; and 4,776,353, which are hereby incorporated herein by reference.

For administration by oral or nasal inhalation, the compounds of the invention are conveniently delivered in the form of an aerosol spray delivered via pressurized packs or a nebulizer, with a suitable propellant, e.g., carbon dioxide or other suitable gas. In the case of a pressurized aerosol, the dosage unit can be controlled by a dose-metered valve. Capsules and cartridges, e.g. gelatin, for use in an inhaler or insufflator can be formulated as a powder mix of the compounds if the invention and a suitable powder base, such as lactose or starch. Formulations adaptable for nasal inhalation of the compounds of the invention are described in U.S. Pat. Nos. 5,935,604 and 5,564,442, which are hereby incorporated herein by reference.

The compounds of the invention can be formulated for parenteral administration by injection, e.g., by bolus injection or continuous infusion. Formulations for injection can be presented in unit-dosage form, e.g., in ampoules or in multidose containers, optionally with an added preservative. The compositions can take such forms as suspensions, solutions, or emulsions in oily or aqueous vehicles, and can contain formulatory agents, such as suspending, stabilizing, or dispersing agents.

Pharmaceutical formulations for parenteral administration include aqueous solutions of the compounds of the invention in water-soluble form. Additionally, suspensions of the compounds of the invention can be prepared as appropriate oily-injection suspensions. Suitable lipophilic solvents or vehicles include fatty oils, such as sesame oil, or synthetic-fatty-acid esters, such as ethyl oleate or triglycerides, or liposomes. Aqueous-injection suspensions can contain substances that increase the viscosity of the suspension, such as sodium carboxymethylcellulose, sorbitol, or dextran. Optionally, the suspension can contain suitable stabilizers or agents that increase the solubility of the compounds of the invention to allow for the preparation of highly concentrated solutions.

Alternatively, the compounds of the invention can be in powder form for constitution with a suitable vehicle, e.g., sterile pyrogen-free water, before use.

The compounds of the invention can also be formulated in rectal compositions, such as suppositories or retention enemas, e.g., containing conventional suppository bases, such as cocoa butter or other glycerides.

The pharmaceutical compositions also can comprise suitable solid- or gel-phase carriers or excipients. Examples of such carriers or excipients include, but are not limited to, calcium carbonate, calcium phosphate, various sugars, starches, cellulose derivatives, gelatin, and polymers, such as polyethylene glycols.

Effective Dosages

Pharmaceutical preparations suitable for use with the present invention include compositions wherein the compounds of the invention are present in effective amounts, i.e., in amounts effective to achieve the intended purpose, for example, neuroprotection, or prevention, treatment or reversal of neuronal dysfunction. Of course, the actual amounts of the compounds of the invention effective for a particular application and the timing of administration will depend upon a variety of factors including, inter alia, the condition being treated, the presence of other concurrent diseases or disorders, the age, weight, general health of the subject, and, where appropriate, the judgment of the prescribing physician. For example, when administered as a neuroprotectant, such compositions will contain amounts of compounds of the invention effective to provide neuroprotection. When administered to enhance memory, prevent or reverse memory decline, prevent or reverse loss of motor function, prevent injury from exposure to organophosphate nerve agents such compositions will contain amounts of compounds of the invention effective to achieve these results. Determination of effective amounts and timing of administration is well within the capabilities of those skilled in the art, especially in light of the detailed-disclosure herein. The dosages given below are a guideline and those skilled in the art may optionally titrate doses or use graded doses of an agent to achieve desired activity and minimize side effects in a treated subject. For example, when treatment is given on a daily basis over a period of time, side effects can be minimized by starting at lower than the target dose of a specific cholinesterase inhibitor maintaining said dose for a period of approximately 2-6 weeks then escalating to a higher dose. This escalation regimen can be repeated multiple times to reach the target dose with minimal incidence of side effects.

The compounds of the invention can be administered adjunctively in any manner that achieves the requisite therapeutic or prophylactic effect. Therapeutically or prophylactically effective doses of the compounds of the invention can be determined from in vitro, animal or human data for analogous compounds that are known to exhibit similar pharmacological activities. The applied doses can be adjusted based on the relative bioavailability, potency and in vivo half-life of the administered compounds as compared with these other agents. The applied doses can be further adjusted based on the anticipated pharmacological effects contributed by each of the compounds of the invention. For example, cholinolytic effects of anticholinergic compounds can permit the use of higher doses of acetylcholinesterase inhibitors or reduce cholinergic side effects. Adjusting the dose to achieve maximal efficacy in humans based on the methods described above and other methods that are well known is well within the capabilities of the ordinarily skilled artisan.

While not intending to be bound by any particular theory of operation, it is believed that the compounds of the invention exert their neuroprotective effects via different and potentially complementary mechanisms of action. A broad spectrum of neuroprotective mechanisms have been associated with huperzine A including acting as an NMDA receptor antagonist, preventing apoptosis, reducing oxidative stress, and normalizing. oxidative metabolism.

Also, although (−)-huperzine A is approximately 50 times more potent than (+)-huperzine A at inhibiting AChE, both enantiomers block the NMDA calcium ion channel with equal potency. Therefore, when proportionately greater NMDA inhibition is preferred, the (+)-huperzine compounds can be selected over (−)-huperzine compounds. In contrast to huperzine A, donepezil bocks the NMDA sodium ion channel.

It has been suggested that huperzine A acts as an NMDA receptor antagonist by either non-competitively binding to a location close to the MK-801 and PCP binding sites in the NMDA calcium ion channel or by acting as an inverse agonist by binding to one of the polyamine regulatory sites on the NMDA receptor. In contrast to huperzine A, caramiphen acts as an NMDA antagonist by interacting with the $Zn^{2+}$ regulatory site on the NMDA receptor, a site distinct from those proposed for huperzine A. Additionally, it has been suggested that diazepam and midazolam may decrease accumulation or production of excitatory amino acids following injury.

Combinations of huperzine A with caramiphen would therefore act upon the NMDA receptor at two potentially complementary sites. This blockade of glutamate induced injury or dysfunction at the receptor level can be further enhanced through the use of agents such as diazepam and midazolam that reduce elevated glutamate levels.

Typically, dosages are in the range of 0.1 µg/kg/day to 100,000 µg/kg/day for huperzine compounds, pharmaceutically acceptable salts or hydrates. Doses for administration of the huperzine compounds, pharmaceutically acceptable salts and hydrates described herein preferably range from about 0.25 to 50,000 µg/kg/day, more preferably, in the range of about 1.25 to 5,000 µg/kg/day.

Typically, dosages are in the range of 0.1 µg/kg/day to 25,000 µg/kg/day for (−)-huperzine compounds, pharmaceutically acceptable salts or hydrates. Doses for administration of the (−)-huperzine compounds, pharmaceutically acceptable salts and hydrates described herein preferably range from about 0.25 to 5,000 µg/kg/day, more preferably, in the range of about 1.25 to 500 µg/kg/day.

Typically, dosages are in the range of 0.2 µg/kg/day to 50,000 µg/kg/day for (±)-huperzine compounds, pharmaceutically acceptable salts or hydrates. Doses for administration of the (±)-huperzine compounds, pharmaceutically acceptable salts and hydrates described herein preferably range from about 0.5 to 10,000 µg/kg/day, more preferably, in the range of about 2.5 to 1,000 µg/kg/day.

Typically, dosages are in the range of 1.0 µg/kg/day to 100,000 µg/kg/day for (+)-huperzine compounds, pharmaceutically acceptable salt or hydrate. Doses for administration of the (+)-huperzine compounds, pharmaceutically acceptable salts and hydrates described herein preferably range from about 2.5 to 50,000 µg/kg/day, more preferably, in the range of about 12.5 to 5,000 µg/kg/day.

Typically, dosages are in the range of 0.1 µg/kg/day to 2,500 µg/kg/day for (−)-huperzine A, pharmaceutically acceptable salts or hydrates. Doses for administration of (−)-huperzine A, pharmaceutically acceptable salts and hydrates described herein preferably range from about 0.25 to 500 µg/kg/day, more preferably, in the range of about 1.25 to 50 µg/kg/day.

Typically, dosages are in the range of 0.2 µg/kg/day to 5,000 µg/kg/day for (±)-huperzine A, pharmaceutically acceptable salts or hydrates. Doses for administration of (±)-huperzine A, pharmaceutically acceptable salts and hydrates described herein preferably range from about 0.5 to 1,000 µg/kg/day, more preferably, in the range of about 2.5 to 100 µg/kg/day.

Typically, dosages are in the range of 1.0 µg/kg/day to 100,000 µg/kg/day for (+)-huperzine A, pharmaceutically acceptable salt or hydrate. Doses for administration of (+)-huperzine A, pharmaceutically acceptable salts and hydrates described herein preferably range from about 2.5 to 20,000 µg/kg/day, more preferably, in the range of about 12.5 to 2,000 µg/kg/day.

Typically, dosages are in the range of 1 µg/kg/day to 25,000 µg/kg/day for (−)-huperzine B, pharmaceutically acceptable salt or hydrate. Doses for administration of (−)-huperzine B, pharmaceutically acceptable salts and hydrates described herein preferably range from about 2.5 to 5000 µg/kg/day, more preferably, in the range of about 12.5 to 500 µg/kg/day.

Typically, dosages are in the range of 2 µg/kg/day to 50,000 µg/kg/day for (O)— huperzine B, pharmaceutically acceptable salt or hydrate. Doses for administration of (±)-huperzine B, pharmaceutically acceptable salts and hydrates described herein preferably range from about 5.0 to 10,000 μg/kg/day, more preferably, in the range of about 25 to 1,000 μg/kg/day.

Typically, dosages are in the range of 10 μg/kg/day to 100,000 μg/kg/day for (+)-huperzine B, pharmaceutically acceptable salt or hydrate. Doses for administration of (+)-huperzine B, pharmaceutically acceptable salts and hydrates described herein preferably range from about 25 to 50,000 μg/kg/day, more preferably, in the range of about 125 to 5,000 μg/kg/day.

Typically, dosages are in the range of 0.1 μg/kg/day to 2,500 μg/kg/day for (−)-10,10-dimethyl huperzine A, pharmaceutically acceptable salts or hydrates. Doses for administration of (−)-10,10-dimethyl huperzine A, pharmaceutically acceptable salts and hydrates described herein preferably range from about 0.25 to 500 μg/kg/day, more preferably, in the range of about 1.25 to 50 μg/kg/day.

Typically, dosages are in the range of 0.2 μg/kg/day to 5,000 μg/kg/day for (±)-10,10-dimethyl huperzine A, pharmaceutically acceptable salts or hydrates. Doses for administration of (±)-10,10-dimethyl huperzine A, pharmaceutically acceptable salts and hydrates described herein preferably range from about 0.5 to 1,000 μg/kg/day, more preferably, in the range of about 2.5 to 100 μg/kg/day.

Typically, dosages are in the range of 10 μg/kg/day to 100,000 μg/kg/day for (+)-10,10-dimethyl huperzine A, pharmaceutically acceptable salt or hydrate. Doses for administration of (+)-10,10-dimethyl huperzine A, pharmaceutically acceptable salts and hydrates described herein preferably range from about 25 to 50,000 μg/kg/day, more preferably, in the range of about 125 to 5,000 μg/kg/day.

Typically, dosages are in the range of 0.1 μg/kg/day to 2,500 μg/kg/day for (−)-HUPFD-13, pharmaceutically acceptable salts or hydrates. Doses for administration of (−)-HUPFD-13, pharmaceutically acceptable salts and hydrates described herein preferably range from about 0.25 to 500 μg/kg/day, more preferably, in the range of about 1.25 to 50 μg/kg/day.

Typically, dosages are in the range of 0.2 μg/kg/day to 5,000 μg/kg/day for (O)—HUPFD-13, pharmaceutically acceptable salts or hydrates. Doses for administration of (±)-HUPFD-13, pharmaceutically acceptable salts and hydrates described herein preferably range from about 0.5 to 1,000 μg/kg/day, more preferably, in the range of about 2.5 to 100 μg/kg/day.

Typically, dosages are in the range of 1.0 μg/kg/day to 100,000 μg/kg/day for (+)-HUPFD-13, pharmaceutically acceptable salt or hydrate. Doses for administration of (+)-HUPFD-13, pharmaceutically acceptable salts and hydrates described herein preferably range from about 2.5 to 20,000 μg/kg/day, more preferably, in the range of about 12.5 to 2,000 μg/kg/day.

Typically, dosages are in the range of 0.2 μg/kg/day to 5,000 μg/kg/day for (−)-huperzine C, (−)-huperzine D, (−)-huperzine G, (−)-huperzinine, (±)-huperzine C, (±)-huperzine D, (±)-huperzine G or (±)-huperzinine, pharmaceutically acceptable salts or hydrates. Doses for administration of (−)-huperzine C, (−)-huperzine D, (−)-huperzine G, or (−)-huperzinine, pharmaceutically acceptable salts and hydrates described herein preferably range from about 0.5 to 1,000 μg/kg/day, more preferably, in the range of about 2.0 to 100 μg/kg/day.

Typically, dosages are in the range of 1.0 μg/kg/day to 100,000 μg/kg/day for (+)-huperzine C, (+)-huperzine D, (+)-huperzine G or (+)-huperzinine, pharmaceutically acceptable salt or hydrate. Doses for administration of (+)-huperzine C, (+)-huperzine D, (+)-huperzine G or (+)-huperzinine, pharmaceutically acceptable salts and hydrates described herein preferably range from about 2.5 to 20,000 μg/kg/day, more preferably, in the range of about 12.5 to 2,000 μg/kg/day.

Typically, dosages are in the range of 1.0 μg/kg/day to 25,000 μg/kg/day for (±)-donepezil A, pharmaceutically acceptable salts or hydrates. Doses for administration of (±)-donepezil A, pharmaceutically acceptable salts and hydrates described herein preferably range from about 2.5 to 5,000 μg/kg/day, more preferably, in the range of about 12.5 to 500 μg/kg/day.

Typically, dosages are in the range of 2.0 μg/kg/day to 50,000 μg/kg/day for (−)-galanthamine, pharmaceutically acceptable salts or hydrates. Doses for administration of (−)-galanthamine, pharmaceutically acceptable salts and hydrates described herein preferably range from about 5.0 to 10,000 μg/kg/day, more preferably, in the range of about 25 to 1,000 μg/kg/day.

Typically, dosages are in the range of 1.0 μg/kg/day to 25,000 μg/kg/day for rivastigmine, pharmaceutically acceptable salts or hydrates. Doses for administration of rivastigmine, pharmaceutically acceptable salts and hydrates described herein preferably range from about 2.5 to 5,000 μg/kg/day, more preferably, in the range of about 12.5 to 500 μg/kg/day.

Typically, dosages are in the range of 10 μg/kg/day to 100,000 μg/kg/day for tacrine, pharmaceutically acceptable salts or hydrates. Doses for administration of tacrine, pharmaceutically acceptable salts and hydrates described herein preferably range from about 25 to 50,000 μg/kg/day, more preferably, in the range of about 125 to 5,000 μg/kg/day.

Typically, dosages are in the range of 0.02 μg/kg/day to 500 μg/kg/day for bis(7)-tacrine, pharmaceutically acceptable salts or hydrates. Doses for administration of bis(7)-tacrine, pharmaceutically acceptable salts and hydrates described herein preferably range from about 0.05 to 100 μg/kg/day, more preferably, in the range of about 0.25 to 10 μg/kg/day.

Typically, dosages are in the range of 0.005 mg/kg/day to 100 mg/kg/day for atropine, pharmaceutically acceptable salts or hydrates. Doses for administration of atropine, pharmaceutically acceptable salts and hydrates described herein preferably range from about 0.02 to 30 mg/kg/day, more preferably, in the range of about 0.1 to 3.0 mg/kg/day.

Typically, dosages are in the range of 0.0025 mg/kg/day to 50 mg/kg/day for scopolamine, pharmaceutically acceptable salts or hydrates. Doses for administration of scopolamine, pharmaceutically acceptable salts and hydrates described herein preferably range from about 0.01 to 15 mg/kg/day, more preferably, in the range of about 0.04 to 1.6 mg/kg/day.

Typically, dosages are in the range of 0.02 mg/kg/day to 350 mg/kg/day for benactyzine, pharmaceutically acceptable salts or hydrates. Doses for administration of benactyzine, pharmaceutically acceptable salts and hydrates described herein preferably range from about 0.06 to 120 mg/kg/day, more preferably, in the range of about 0.3 to 12 mg/kg/day.

Typically, dosages are in the range of 0.02 mg/kg/day to 300 mg/kg/day for caramiphen, pharmaceutically acceptable salts or hydrates. Doses for administration of caramiphen, pharmaceutically acceptable salts and hydrates described herein preferably range from about 0.05 to 100 mg/kg/day, more preferably, in the range of about 0.25 to 10 mg/kg/day.

Typically, dosages are in the range of 0.01 mg/kg/day to 200 μg/kg/day for trihexyphenidyl, pharmaceutically acceptable salts or hydrates. Doses for administration of trihexyphenidyl, pharmaceutically acceptable salts and hydrates described herein preferably range from about 0.02 to 25 mg/kg/day, more preferably, in the range of about 0.1 to 4 mg/kg/day.

Typically, dosages are in the range of 0.01 mg/kg/day to 160 mg/kg/day for diazepam, pharmaceutically acceptable salts or hydrates. Doses for administration of diazepam, pharmaceutically acceptable salts and hydrates described herein preferably range from about 0.02 to 40 mg/kg/day, more preferably, in the range of about 0.2 to 8 mg/kg/day.

Typically, dosages are in the range of 0.01 mg/kg/day to 160 mg/kg/day for midazolam, pharmaceutically acceptable salts or hydrates. Doses for administration of midazolam, pharmaceutically acceptable salts and hydrates described herein preferably range from about 0.02 to 40 mg/kg/day, more preferably, in the range of about 0.2 to 8 mg/kg/day.

Transdermal patches for daily administration of huperzine compounds, pharmaceutically acceptable salts and hydrates will typically comprise from about 5 μg to 1,500 μg huperzine compound, pharmaceutically acceptable salt or hydrate. Transdermal patches are commercially available for scopolamine and can be prepared for other compounds of the invention by those skilled in the art. Preferably, a single transdermal patch will include a huperzine compound, at least one anticholinergic compound and an anticonvulsive compound.

In one embodiment the compounds of the invention are typically administered as part of a daily regimen, regardless of the mode of administration. As part of a daily regiment, the compounds may be administered once per day or more than once per day. In another embodiment, e.g., protection against nerve agents or protection against neurologic complications of cardiac surgery, the compounds of the invention may be administered as a single dose or multiple doses prior to exposure to nerve agent or surgery, respectively.

Where two or more compounds of each class are administered (e.g., huperzine A and huperzine B), the above-delineated dosage ranges refer to the total dosage of the particular class of compound which may be adjusted proportionately to reflect the relative potencies of each compound of the class. For example, the combination of 250 μg (−)-huperzine A and 2.5 mg (−)-huperzine B would produce approximately the same AChE inhibition as 500 μg (−)-huperzine A. Another example would be the combination of 250 μg (−)-huperzine A and 12.5 mg (+)-huperzine A, which would produce approximately the same AChE inhibition as 500 μg (−)-huperzine A.

Depending upon the neuroprotective effect desired, the compounds of the invention can be adjunctively administered to achieve either a therapeutic or a prophylactic effect. For example, the compounds of the invention can be prophylactically adjunctively administered to a healthy young, middle-aged or elderly subject who has not yet suffered age-related neuronal dysfunction, such as cognitive decline in order to protect against such declines, or even to therapeutically enhance cognition or abilities to perform complex tasks, including, for example, concentration (focus) or memory acquisition, storage or retrieval. Alternatively, the compounds of the invention can be adjunctively administered to older subjects who have suffered age-related neuronal dysfunction, such as declines in cognitive function, to prophylactically protect against further age-related cognitive decline, or to improve cognitive function.

Uses of the compositions of the invention and methods of the invention for (±) the prevention and/or treatment of diseases and disorders of the central nervous system and/or the peripheral nervous system, (ii) the prevention and/or treatment of neuronal dysfunction and/or degenerative changes caused by injury to the central nervous system and/or peripheral nervous system, and/or (iii) improving cognitive functions and/or neuromuscular functions are shown in Table 2. The skilled artisan will recognize that there are alternative nomenclatures, nosologies, and classification systems for pathologic diseases, disorders and conditions and that these systems evolve with medical scientific progress.

TABLE 2

| Description of disease, disorder, or other use | Treatment effect or treatment effect evident on:[1] | Drug Targets | | Composition or method of treatment | | |
|---|---|---|---|---|---|---|
| | | Functional | Neuroprotective | (a) | (a)(b) | (a)(b)(c) |
| age-associated cognitive decline | neuroprotection memory cognition | AChE[2] | oxidative stress | +[5] | | |
| age-associated memory impairment | neuroprotection memory | AChE | oxidative stress | + | | |
| AIDS dementia | neuroprotection memory mental concentration | AChE | NMDA[3] AMPA[4] apoptosis | + | ++[6] | ++ |
| alcoholism | neuroprotection craving withdrawal - seizures | NMDA AMPA | NMDA AMPA oxidative stress | + | ++ | +++[7] |
| Alzheimer's disease | neuroprotection memory cognition behavior | AChE NMDA | NMDA AMPA apoptosis oxidative stress | + | ++ | +++ |
| amyotrophic lateral sclerosis | neuroprotection muscle strength muscle atrophy | AChE | NMDA AMPA oxidative stress apoptosis | + | ++ | +++ |
| anxiety[8] | anxiety symptoms[8] | AChE NMDA AMPA | | + | ++ | +++ |
| anxiety disorders[9] | anxiety disorder symptoms[9] | AChE NMDA AMPA | | + | ++ | +++ |
| attention deficit disorder | cognition attention | AChE | | + | | |

TABLE 2-continued

| Description of disease, disorder, or other use | Treatment effect or treatment effect evident on:[1] | Drug Targets | | Composition or method of treatment | | |
|---|---|---|---|---|---|---|
| | | Functional | Neuroprotective | (a) | (a)(b) | (a)(b)(c) |
| attention deficit hyperactivity disorder | cognition attention hyperactivity | AChE AMPA | | + | + | |
| cocaine addiction | craving withdrawal | NMDA AMPA | | + | + | |
| Creutzfeld-Jacob disease | neuroprotection memory muscle strength | AChE | NMDA apoptosis | ++ | ++ | + |
| CNS incapacitating agents[13] | cognition delusions | AChE | | + | | |
| depression | depression | NMDA | | + | + | |
| Down syndrome | neuroprotection cognition language skills | AChE | oxidative stress apoptosis | + | | |
| eating disorders[10] | compulsive behavior craving | NMDA AMPA | | + | ++ | |
| epilepsy | neuroprotection seizures memory | AChE | NMDA AMPA | + | ++ | +++ |
| glaucoma | neuroprotection vision intraocular pressure | AChE | NMDA AMPA | + | ++ | ++ |
| headache - migraine | pain | AChE NMDA | | + | + | |
| hepatic encephalopathy | neuroprotection memory mental concentration attention | AChE | NMDA AMPA ox metabolism | + | ++ | +++ |
| Huntington's disease | neuroprotection memory cognition | AChE | NMDA AMPA apoptosis oxidative stress ox metabolism | + | ++ | +++ |
| hyperalgesia | pain | NMDA AMPA | | + | ++ | +++ |
| hypoxic-ischemic encephalopathy[11] | neuroprotection memory cognition seizures | AChE | NMDA AMPA apoptosis oxidative stress | + | ++ | +++ |
| Lewy body dementia | neuroprotection memory cognition | AChE | NMDA AMPA apoptosis oxidative stress | + | ++ | +++ |
| memory and cognitive improvement in healthy individuals | neuroprotection memory cognition | AChE | oxidative stress | + | | |
| mild cognitive impairment | neuroprotection memory cognition | AChE | NMDA AMPA apoptosis oxidative stress | + | ++ | +++ |
| multiple sclerosis | neuroprotection memory attention mental concentration muscle strength | AChE | NMDA AMPA | + | ++ | +++ |
| myasthenia gravis | muscle strength | AChE | | + | + | |
| neurogenic orthostatic hypotension | blood pressure | AChE | | + | + | |
| neurologic complications of cardiac surgery | neuroprotection memory | AChE | NMDA AMPA | + | ++ | +++ |
| neuromuscular block | muscle function | AChE | | + | | |
| nicotine addiction | craving | NMDA | | + | ++ | |
| obsessive compulsive disorder | craving | NMDA AMPA | | + | ++ | ++ |

TABLE 2-continued

| Description of disease, disorder, or other use | Treatment effect or treatment effect evident on:[1] | Drug Targets | | Composition or method of treatment | | |
|---|---|---|---|---|---|---|
| | | Functional | Neuroprotective | (a) | (a)(b) | (a)(b)(c) |
| olivopontocerebellar atrophy | neuroprotection memory cognition muscle strength | AChE | NMDA AMPA | + | ++ | +++ |
| opiate addiction | | NMDA AMPA | | + | ++ | ++ |
| organophosphate insecticide poisoning | neuroprotection survival convulsions memory | | AChE NMDA AMPA oxidative stress | + | ++ | +++ |
| organophosphate nerve agent poisoning | neuroprotection survival convulsions memory | | AChE NMDA AMPA oxidative stress | + | ++ | +++ |
| pain - acute | pain | AMPA | | + | ++ | ++ |
| pain - chronic | pain | NMDA AMPA | | + | ++ | ++ |
| Parkinson's disease | neuroprotection memory cognition | AChE | NMDA AMPA apoptosis oxidative stress | + | ++ | +++ |
| peripheral nerve injury | | | NMDA AMPA | + | ++ | ++ |
| post-polio syndrome | neuroprotection muscle strength | AChE | oxidative metabolism | + | ++ | |
| psychomotor skill improvement in healthy individuals | performance of complex tasks | AChE | | + | | |
| retinal diseases[12] | neuroprotection vision | | NMDA AMPA apoptosis | + | ++ | +++ |
| Rett syndrome | neuroprotection cognition muscle strength seizures | AChE | AMPA NMDA apoptosis oxidative stress | + | ++ | +++ |
| schizophrenia | memory cognition | AChE | (−) NMDA (−) AMPA | + | | |
| seizure disorders | neuroprotection seizures convulsions | | NMDA AMPA | + | ++ | +++ |
| spasticity | dystonic movement | NMDA | | + | ++ | ++ |
| spinal cord injury | neuroprotection muscle strength | AChE | NMDA AMPA | + | ++ | +++ |
| stroke - acute | neuroprotection memory | AChE | NMDA AMPA apoptosis oxidative stress ox metabolism | + | ++ | +++ |
| tardive dyskinesia | neuroprotection dystonic movement | AChE | NMDA oxidative stress | + | ++ | +++ |
| tinnitus | neuroprotection hearing | | NMDA AMPA | + | ++ | +++ |
| transient ischemic attack | neuroprotection | AChE | NMDA AMPA | + | ++ | +++ |
| traumatic brain injury | neuroprotection memory cognition | AChE | NMDA AMPA apoptosis oxidative stress | + | ++ | +++ |
| vascular dementia | neuroprotection memory cognition | AChE | NMDA AMPA oxidative stress | + | ++ | +++ |

TABLE 2-continued

| Description of disease, disorder, or other use | Treatment effect or treatment effect evident on:[1] | Drug Targets | | Composition or method of treatment | | |
|---|---|---|---|---|---|---|
| | | Functional | Neuroprotective | (a) | (a)(b) | (a)(b)(c) |
| Wernicke-Korsakoff syndrome | memory cognition | AChE | | + | | |

[1]"Treatment effect on" memory, cognition, mental concentration, craving, seizures, behavior, anxiety, attention, muscle strength, muscle atrophy, language skills, hyperactivity, withdrawal, compulsive behavior, pain, blood pressure, survival, convulsions, performance of complex tasks, vision, dystonic movement, involuntary movement, hearing means that in connection with treatment of the co-described disease, disorder or other use there is a favorable outcome determinable by established clinical criteria on the referenced parameter. Some of these treatment effects are illustrated without limitation by the following examples: In relation to memory, "treatment effect on" refers to without limitation: (i) preventing memory impairment from occurring in a subject which may be predisposed to memory impairment but has not yet been diagnosed as having it; (ii) inhibiting memory impairment, i.e., arresting its development; (iii) reversing memory impairment, i.e., causing its regression; and/or (iv) improving memory. In relation to cognition, "treatment effect on" refers to without limitation: (i) preventing cognitive impairment from occurring in a subject which may be predisposed to cognitive impairment but has not yet been diagnosed as having it; (ii) inhibiting cognitive impairment, i.e., arresting its development; (iii) reversing cognitive impairment, i.e., causing its regression; and/or (iv) improving cognition. In relation to muscle strength, "treatment effect on" refers to without limitation: (i) preventing loss of muscle strength from occurring in a subject which may be redisposed to developing muscle weakness but has not yet been diagnosed as having it; (ii) inhibiting loss of muscle strength, i.e., arresting its development; (iii) reversing muscle weakness, i.e., causing its regression; and/or (iv) improving neuromuscular function.
[2]Acetylcholinesterase.
[3]NMDA receptor.
[4]AMPA receptor.
[5]Preferred.
[6]More Preferred.
[7]Most Preferred.
[8]"Anxiety" includes without limitation the unpleasant emotion state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. Dorland's Illustrated Medical Dictionary, W. B. Saunders Co., 27th ed. (1988).
[9]"Anxiety disorder" includes without limitation mental disorders in which anxiety and avoidance behavior predominate. Dorland's Illustrated Medical Dictionary, W. B. Saunders Co., 27th ed. (1988). Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in Diagnostic and Statistical Manual of Mental Disorders (American Psychiatric Association 4th ed. 1994).
[10]"Eating disorders" includes anorexia nervosa and bulimia.
[11]"Hypoxic-ischemic encephalopathy" includes hypoxia, hypoxia-ischemia, perinatal asphyxia and reperfusion injury.
[12]"Retinal disease" includes retinal ischemia, retinitis pigmentosa, and diabetic retinopathy.
[13]"CNS incapacitating agents" are anticholinergic chemical agents that produce reversible disturbances in the central nervous system that disrupt cognitive ability producing confusion, disorientation, and impaired perception. These agents include 3-quinuclidinyl benzilate (BZ), agent 15, atropine, scopolamine and anticholinergic histamines.

EXAMPLES

Example 1

Protection Against the Toxic Effects of Organophosphate Nerve Agents and Organophosphate Insecticides There is an urgent need for countermeasures that are effective, safe and practical to save lives and prevent injury in the event of an attack with organophosphate (OP) nerve agents on civilian and military populations. The current FDA approved therapeutic regimen uses an oral antidote enhancer, pyridostigmine bromide (PB), in combination with a two-part injectable antidote consisting of an anticholinergic drug, atropine (ATR), and a cholinesterase reactivator, 2-pralidoxime (2-PAM) that can protect against lethality to some extent, but not the severe incapacitation that can result from nerve agent exposure. Because PB and 2-PAM do not cross the blood-brain barrier, this regimen partially protects the peripheral nervous system, but not the central nervous system (CNS). The safety and efficacy of this regimen requires precise timing of dosing. In the case of soman, to be effective the antidote (ATR and 2-PAM) must be injected immediately after exposure. On the other hand, if the antidote is given in the absence of exposure, an atropine overdose may result requiring medical intervention.

Huperzine A, a potent acetylcholinesterase (AChE) inhibitor with high bioavailability in both peripheral and central nervous systems has been shown to protect rodents and monkeys from soman poisoning. In addition to shielding the enzymatic site of AChE, huperzine A offers additional protective mechanisms by acting as an N-methyl-D-aspartate (NMDA) receptor antagonist and by reducing apoptosis and oxidative stress and normalizing oxidative metabolism. By combining huperzine A with compounds with anticholinergic, anti-glutamatergic and/or anticonvulsant properties this protection can be substantially enhanced.

The first OP nerve agents were discovered by German scientists conducting pesticide research in the period before World War II leading to Germany's development of G series nerve agents during the war years. After the war American and British scientists developed V series nerve agents, a second generation of more toxic and persistent compounds. Beginning in the 1980s, Soviet scientists developed a third generation of new and more lethal nerve agents including a variant of VX, referred to as VR, V-gas or substance 33, and the Novichok series. The most widely produced OP nerve agents include tabun (GA), sarin (GB), soman (GD), VR and VX. Nerve agents have been produced and stockpiled by many nations around the globe and there is evidence that terrorist organizations have developed crude procedures for making sarin, and VX.

There is only one documented use of a nerve agent in wartime, i.e., the use of GF (cyclosarin) by Iraq in the Iraq-Iran war. On the other hand, nerve agents have already been used three times against civilian populations. The Iraqi government used cyclosarin against its own citizens in March 1988, and the Aum Shinrikyo cult in Japan used crude preparations of sarin in 1994 and 1995 in public places in Japan. In 1994, the Aum Shinrikyo attacked an apartment complex in Matsumoto, Japan, killing 7 people and sending 280 to the hospital. On Mar. 20, 1995, the Aum Shinrikyo cult carried out an attack on the Tokyo subway system resulting in 12 dead and 5,510 treated.

Another threat is the use of organophosphate insecticides, which can act as low-grade nerve agents, as weapons. In contrast to military grade nerve agents, which involve the use of banned substances such as sarin and soman, organophosphate insecticides are usually readily (and legally) available in connection with agricultural operations. Some of the most common of these are organophosphate insecticides can act as low-grade nerve agents.

Additionally, OP agricultural pesticides have been reported by the World Health Organization (WHO) to be responsible for more than 3 million unintentional poisonings including 200,000 deaths annually worldwide. In the United States, 4002 cases of symptomatic illnesses attributed to exposure to organophosphate pesticides were reported to Poison Control Centers for 1996. Approximately 3 dozen commercially available insecticides are considered highly toxic with oral $LD_{50}$s in rats less than or equal to 50 mg/kg. These include azinphos-methyl (Gusathion, Guthion), bornyl (Swat), dimefos (Hanane, Pestox XIV), methamidophos (Supracide, Ultracide), and methyl parathion (E 601, Penncap-M) among others.

OP agents exert their acute toxic effects mainly through their ability to rapidly and irreversibly inhibit central and peripheral acetylcholinesterases. Since this enzyme is responsible for the hydrolysis of acetylcholine (ACh), such inhibition causes the accumulation of excessive ACh concentrations at nerve synapses and neuromuscular junctions including the endings of the parasympathetic nerves to the smooth muscle of the iris, ciliary body, bronchial tree, gastrointestinal tract, bladder and blood vessels; to the salivary glands and secretory glands of the gastrointestinal tract and respiratory tract; and to the cardiac muscle; the endings of sympathetic nerves to the sweat glands; and the endings of motor neurons to skeletal muscles. This causes a persistent, over-stimulation of cholinergic receptors followed by receptor fatigue. The clinical effects of nerve agents are the result of this persistent stimulation and subsequent fatigue at the ACh receptor as evidenced by muscle fasciculations, fatigue and paralysis, increased secretions, respiratory depression, cardiovascular irregularities, and CNS changes including seizures and coma, behavioral and psychological changes and mental impairment. Injury to the nervous system is amplified by the excitotoxic activity of glutamate released following the initial pathological rise in ACh levels, as well as by hypoxic and free radical mechanisms.

Following exposure to lethal OP agent concentrations, death is believed to result primarily from respiratory failure due to the accumulation of ACh 1) at nicotinic receptors at the neuromuscular junction, resulting in pathological stimulation and ultimate failure of the muscles of respiration, 2) at muscarinic receptors in secretory glands and smooth muscle, resulting in excessive respiratory secretions and bronchoconstriction, and 3) at cholinergic receptors in the brain, resulting in central respiratory depression.

Exposure to non-lethal OP concentrations may produce long-term CNS impairment or dysfunction lasting weeks to several months, or possibly several years. Behavioral changes and cognitive incapacitations, such as impaired learning and memory have been observed in humans and animals and are associated with neuronal degeneration of hippocampal structures.

Although the current therapeutic regimen for treating acute OP agent exposure can be effective at preventing fatalities if administered in an appropriate time frame, it suffers from several important disadvantages including:
  a. It does not adequately protect the CNS and therefore does not prevent the occurrence of severe post-exposure incapacitation including substantial behavioral impairment, performance deficits, and convulsions, or, in many cases, permanent brain damage;
  b. The efficacy of atropine and oxime treatment demands precise timing and sequencing of drug administration at the time of OP exposure, which, while practical under laboratory conditions, is very difficult to execute in reality;
  c. Some nerve agents, e.g., GA (tabun), resist oxime reactivation of AChE making treatment very difficult; and
  d. The pretreatment agent pyridostigmine bromide (PB):
    i. gives no protection by itself;
    ii. is effective in enhancing the efficacy of atropine and oxime treatment against soman and tabun, reduces efficacy against sarin and VX, gives no clear benefit against GF and had no effect on efficacy against VR;
    iii. may exacerbate the effects of a sub-lethal exposure to soman; and
    iv. must be taken continuously throughout a period of heightened risk, because if taken shortly before or at the time of exposure is not expected to be effective. In fact, studies in monkeys showed that PB given less than 3 hours prior to soman exposure resulted increased levels of AChE inhibition raising the prospects of worsening the effects of exposure to soman or other OP agents within this time period.

Review of Soman Protection Data for (−)-Huperzine A (−)-Huperzine A is a plant-based alkaloid extracted from *Huperzia serrata*, a club moss that is native to China. It is also present in a related North American club moss, *Lycopodium selago* (ESTHER Database). Huperzine A is a potent, reversible, mixed competitive inhibitor of AChE with high affinity for AChE (Ki=20-40 nM), and a slow rate of dissociation from the enzyme ($t_{0.5}$=35 minutes). Clinical and animal studies with huperzine A have demonstrated excellent pharmacological characteristics including rapid adsorption, high bioavailability, efficient penetration of the blood brain barrier and a long half-life.

Known chemically as (5R,9R,11E)-5-amino-11-ethylidene-5,6,9-10-tetrahydro-77-methyl-5,9-methanocyclooctа (b) pyridin-2(1H)-1, huperzine A has an empirical formula of $C_{15}H_{18}N_2O$ and a molecular weight of 242.32. The complete synthesis of huperzine A has been reported. Unless otherwise stated, all references to huperzine A in this document shall mean (−)-huperzine A. The structural formula for huperzine A is shown in FIG. 1.

In animals, huperzine A has provided protection of both the CNS and peripheral nervous system to approximately 1 $LD_{50}$ soman. In addition to reversibly sequestering the active site of AChE, huperzine A offers additional protective mechanisms including preventing neuronal injury caused by glutamate-induced, N-methyl-D-aspartate (NMDA) receptor-mediated calcium mobilization, dysregulation of oxidative metabolism, free radicals and apoptosis.

Huperzine A has been shown to protect rhesus and cynomolgus monkeys, guinea pigs, rats and mice against lethal doses of soman. Several studies have shown protection to soman following pretreatment with a single injection of huperzine A. At the highest dose tested, 500 μg/kg i.p., cholinergic side effects were evident, but disappeared within 0.5-3 hours.

Four rhesus monkeys challenged with 1-1.3 $LD_{50}$ soman by intravenous injection at intervals between 65 minutes and 14 hours after receiving a single, dose of 50 μg/kg huperzine A by intravenous injection showed only minor toxic signs and survived without any need for post-exposure treatment (Ashani Y., Grunwald J. 1996).

Rodents pretreated with huperzine A 30 minutes prior to challenge with a subcutaneous injection of 2 $LD_{50}$ soman showed a dose dependent decrease in seizures and mortality. All animals were also treated with atropine and 2-PAM one minute after challenge to reduce peripheral toxicity. Seizures were evident in all animals receiving the lowest doses of huperzine A (12.5 μg/kg (4/4 animals) or 31.25 μg/kg (6/6 animals)) and only a single animal in the 31.25 μg/kg group survived until the end of the 24 hour observation period. Anti-seizure activity appeared to plateau at a dose of 125 μg/kg and survival appeared to plateau at a dose of 62.5 μg/kg with at least 83% of the animals free of seizures and surviving until the end of the 24 hour observation period, respectively. At the highest dose of huperzine A (500 μg/kg), 83% of the animals were protected against seizures but only 50% of the animals survived (Ved H., Nguyen T. 2000). In another study, guinea pigs receiving 500 μg/kg huperzine A intraperitoneally were challenged with soman. After challenge, N-methyl atropine was administered to all animals to prevent peripheral toxicities caused by soman. All animals pretreated with huperzine A remained seizure free and survived the 24 hour observation period following soman challenge. At the conclusion of the study, hippocampal tissue from the huperzine A group was free of any signs of neuronal damage (Lallement G., Veyret J. 1997).

Rats exposed to 1 $LD_{50}$ of soman by subcutaneous injection evidenced dose dependant protection against seizures and mortality when treated 2 hours before challenge with a single i.p. injection of either 100 μg/kg or 500 μg/kg huperzine A. Cholinergic side effects that disappeared within 30 minutes were observed in rats receiving the 500 μg/kg huperzine A dose. All animals including all controls received oxime 30 minutes before soman challenge and N-methyl atropine immediately after challenge to limit peripheral effects and respiratory depression. Compared to the control group, deaths were reduced by 60% and 77% and seizure incidence was reduced by 16% and 100% in the groups pretreated with 100 and 500 μg/kg huperzine A (Tonduli L. S., Testylier G. 2001).

Mice challenged with soman after receiving a 500 μg/kg i.p. dose of (±)-huperzine A (the (+)-huperzine A stereoisomer is approximately 100-fold less active as an inhibitor of acetylcholinesterase) maintained a protective ratio of 2 for at least 6 hours without need for any post-challenge therapy. Mild cholinergic toxicity evidenced by transient tremors that disappeared within 2-3 hrs was elicited by the 500 μg/kg i.p. dose (Grunwald J., Raveh L. 1994). When (±)-huperzine A was administered in combination with human butyrylcholinesterase, a promising potential OP agent scavenger, the resulting protective ratio of 2.57 equaled the sum of the individual contribution of each drug (Ashani Y., Grunwald J. 1996).

Enhancing Protection with Combination Therapy

Animal studies offer examples of the ability of huperzine A to protect against soman toxicity at doses in the 1 $LD_{50}$ range. Protection against substantially greater doses of soman and other nerve agents can be achieved through the combined use of huperzine A together with compounds with anticholinergic (cholinolytic) or mixed anticholinergic and antiglutamatergic properties reducing or eliminating the need for post-exposure therapy. Cholinolytic compounds in such combinations allow for use of higher doses of huperzine A without triggering unacceptable cholinergic side effects and reduce cholinergic toxicities caused by nerve agents. Antiglutamatergic activity protect against pathologies associated with excitotoxic levels of glutamate. In preclinical studies, atropine (ATR), an anticholinergic, reduced acute toxicity associated with huperzine A. Another example of reducing cholinergic side effects with ATR, is its use to reduce gastrointestinal side. effects when PB is used in the treatment of myasthenia gravis (PB Package Insert Hoffman-La Roche 1995, Merck Manual 2003).

Anticholinergic drugs including ATR (Berry W. K., Davies D R 1970), caramiphen (CRM) (Raveh L., Chapman S., et al. 1999, Sommer A., Bleyer H. 1994), scopolamine (SCO) (Lallement G., Foquin A. et al. 2001), benactyzine (BNZ) (Sommer A., Bleyer H. 1994, Kassa J., Vachek J. et al. 2001) and trihexyphenidyl (THP) (Kassa J., Vachek J. et al. 2001) have been used adjunctively with varying degrees of success to increase the effectiveness of PB or physostigmine in prophylactic regimens for nerve agents.

One such combination, in which BNZ and THP are used adjunctively with PB (PB•BNZ•THP), has been developed (Krejcova G., Kassa J. 2003). A single oral dose of PB•BNZ•THP (5.82 mg/kg PB, 70 mg/kg BNZ, 16 mg/kg THP) given 120 minutes before challenge protected rats against 1 $LD_{50}$ tabun (280 μg/kg i.m.). In a separate study referenced in Krejcova G, Kassa J 2003, mice and rats pretreated with PB•BNZ•THP were protected against challenge with 2.5 $LD_{50}$ tabun.

CRM (10 mg/kg, s.c.), an anticonvulsant anticholinergic drug with antiglutamatergic properties, used as a pretreatment in combination with PB (0.1 mg/kg, i.m.) reduced brain damage and cognitive deficits and prevented convulsions in rats exposed to 1 $LD_{50}$ soman (Raveh L., Weissman B. A. et al. 2002). In lethality studies, this combination had a protective ratio of approximately 2 (Raveh L., Chapman S., et al. 1999).

Human Clinical Studies

Huperzine A in a tablet formulation was rapidly absorbed following oral administration ($T_{1/2Ka}$=12.6 minutes). On average, peak plasma concentrations were reached after approximately 79.6 minutes. The elimination half-life of huperzine A is approximately 288.5 minutes (Qian B. C., Wang M et al. 1995).

In clinical trials, daily oral doses of 300-400 μg huperzine A reduced memory and cognitive deficits in individuals diagnosed with Alzheimer's disease and age-associated cognitive decline. In addition, myasthenia gravis patients have shown improvement following treatment with huperzine A. At these dose levels huperzine A has been well tolerated with a low incidence of side effects. At higher doses huperzine A has also been shown to reduce memory impairment, but there was also a dose-dependent increase in side effects with approximately 50% of patients in one study showing side effects at 1200 μg/day dose of huperzine A. When side effects have occurred they are generally cholinergic in nature.

Animal Studies

The cholinergic and neuroprotective properties, safety and pharmacokinetics of huperzine A have been studied in a broad range of animals including rodents, rabbits, dogs and non-human primates. These studies have shown effectiveness in improving memory, learning, cognition and neuromuscular transmission; protecting against the toxic effects of organophosphate nerve agents, excitotoxic amino acids and oxygen-glucose deprivation; and have evaluated toxicology and teratogenicity.

In rat studies, huperzine A was well absorbed after oral administration with a relative bioavailability of 96.9%. Peak plasma concentrations were reached at 10-30 minutes after oral administration. Maximal AChE inhibition and ACh elevation of 43% and 40%, respectively, were achieved in the brain 30-60 minutes after intramuscular injection of 2 mg/kg huperzine A. Inhibition of AChE activity and elevation in ACh level declined to 32% and 12%, respectively, at 6 hours post administration (Wang Y. E., Feng, J. 1988).

Huperzine A produced dose-dependant inhibition of brain AChE following oral administration (Cheng, D. H., Tang, X. C. 1998). Acute i.m. administration of huperzine A (2 mg/kg) in rats resulted in up to 6 hours inhibition of brain AChE and an increase in the ACh levels up to 40% at 60 min. Maximal ACh elevation was evident in frontal (125%) and parietal (105%) cortex and smaller increases (22-65%) in other brain regions (Tang, X. C., De Sarno, P 1989).

Multiple neuropathological changes along with cognitive and behavioral deficits are evident in survivors of nerve agent intoxication as well as neurodegenerative disorders including AD and vascular dementia. Neuroprotective benefits of huperzine A have been demonstrated following nerve agent intoxication and in animal models of AD (Wang R., Zhang H. Y. et al. 2001), vascular dementia (Wang L M, Han Y F et al. 2000) and hypoxia-ischemia (Wang L S, Zhou J et al. 2002). Neuroprotection conferred by huperzine A has been associated with multiple mechanisms including reducing oxidative stress (Shang Y Z, Ye J W et al. 1999), improving compromised energy metabolism, reducing apoptosis, antagonizing glutamate-induced, N-methyl-D-aspartate (NMDA) receptor-mediated calcium mobilization (Ved, H. S., Koenig, M. K. et al. 1997, Ved, H., Nguyen, T., et al. 2000) and improving neurotransmitter levels. While some of these protective activities clearly are cholinergically driven, others are not. For example, it has recently been shown that (+)-huperzine A and (−)-huperzine A antagonized the NMDA receptor with similar potency (Zhang, Y. H., Chen X. Q. et al. 2000), although (+)-huperzine A has been reported to be approximately 100-fold less potent than (−)-huperzine A in its ability to inhibit AChE. In addition, both enantiomers showed similar abilities to protect PC12 and NG108-15 cells from B-amyloid injury (Zhang H. Y., Liang Y. Q. et al. 2002).

Citation or identification of any reference in this application is not an admission that such reference is prior art to the present invention.

Tables 3-5 show examples of combinations of active ingredients that can protect an animal subject from the toxic effects of organophosphate nerve agents and organophosphate insecticides. In the following examples, the active ingredients are orally administered to the subject animal 60 minutes prior to challenge with a dose of at least 1 $LD_{50}$ of the OP agent administered by subcutaneous or intramuscular injection in the case of non-human animal subjects or prior to exposure in the case of humans. OP agents that can be used for challenge or for which exposure may occur include nerve agents such as GA (tabun), GB (sarin), GD (soman), GF (cyclosarin), VR, VX, Novichok-5 and Novichok-7, and insecticides such as azinphos-methyl (Gusathion, Guthion), bornyl (Swat), dimefos (Hanane, Pestox XIV), methamidophos (Supracide, Ultracide), and methyl parathion (E601, Penncap-M). To increase protection these combinations can optionally be used in combination with human butyrylcholinesterase at a dose of 30 mg/kg for guinea pigs or 18 mg/kg for monkeys administered by intramuscular injection 45 minutes prior to OP agent challenge. Additionally, to increase protection these combinations can optionally be used in combination with standard post-exposure antidotes including for example ATR and 2-PAM or ATR and HI-6.

TABLE 3

| Subject | Dose of Active Ingredients (mg/kg) | | |
|---|---|---|---|
| Guinea Pig | 0.5 (−)-Hup-A[1] | 15 ATR | |
| Guinea Pig | 0.5 (−)-Hup-A[1] | 15 ATR | 5.0 DZP[3] |
| Guinea Pig | 0.5 (−)-Hup-A[1] | 70 BNZ | 16 THP |
| Guinea Pig | 0.5 (−)-Hup-A[1] | 70 BNZ | 16 THP | 5.0 DZP[3] |
| Guinea Pig | 0.5 (−)-Hup-A[1] | 60 CRM | |
| Guinea Pig | 0.5 (−)-Hup-A[1] | 60 CRM | 5.0 DZP[3] |
| Guinea Pig | 0.5 (−)-Hup-A[1] | 7.5 SCO | |
| Guinea Pig | 0.5 (−)-Hup-A[1] | 7.5 SCO | 5.0 DZP[3] |
| Guinea Pig | 0.1 bis(7)-THA[2] | 15 ATR | |
| Guinea Pig | 0.1 bis(7)-THA[2] | 15 ATR | 5.0 DZP[3] |
| Guinea Pig | 0.1 bis(7)-THA[2] | 70 BNZ | 16 THP |
| Guinea Pig | 0.1 bis(7) THA[2] | 70 BNZ | 16 THP | 5.0 DZP[3] |
| Guinea Pig | 0.1 bis(7)-THA[2] | 60 CRM | |
| Guinea Pig | 0.1 bis(7)-THA[2] | 60 CRM | 5.0 DZP[3] |
| Guinea Pig | 0.1 bis(7)-THA[2] | 7.5 SCO | |
| Guinea Pig | 0.1 bis(7)-THA[2] | 7.5 SCO | 5.0 DZP[3] |

[1](−)-Hup-A is (−)-huperzine A. In the above examples 1.0 mg/kg (±)-huperzine A, 5.0 mg/kg (−)-huperzine B, 10 mg/kg (±)-huperzine B, 0.65 mg/kg (−)-10,10-dimethyl huperzine A, 1.30 mg/kg (±)-10,10-dimethyl huperzine A, 0.5 mg/kg (−)-HUPFD-13, or 1.0 mg/kg (±)-HUPFD-13 can be substituted for (−)-huperzine A.
[2]bis(7)-THA is bis(7)-tacrine. In the above examples 50 mg/kg tacrine, 10 mg/kg (−)-galanthamine, 5 mg/kg rivastigmine or 5 mg/kg donepezil can be substituted for bis(7)-tacrine.
[3]5.0 mg/kg MDZ can be substituted for DZP.

TABLE 4

| Subject | Dose of Active Ingredients (mg/kg) | | |
|---|---|---|---|
| monkey | 0.2 (−)-Hup-A[1] | 3.0 ATR | |
| monkey | 0.2 (−)-Hup-A[1] | 3.0 ATR | 1.0 DZP[3] |
| monkey | 0.2 (−)-Hup-A[1] | 14 BNZ | 3.2 THP |
| monkey | 0.2 (−)-Hup-A[1] | 14 BNZ | 3.2 THP | 1.0 DZP[3] |
| monkey | 0.2 (−)-Hup-A[1] | 15 CRM | |
| monkey | 0.2 (−)-Hup-A[1] | 15 CRM | 1.0 DZP[3] |
| monkey | 0.2 (−)-Hup-A[1] | 1.5 SCO | |
| monkey | 0.2 (−)-Hup-A[1] | 1.5 SCO | 1.0 DZP[3] |
| monkey | 0.04 bis(7)-THA[2] | 3.0 ATR | |
| monkey | 0.04 bis(7)-THA[2] | 3.0 ATR | 1.0 DZP[3] |
| monkey | 0.04 bis(7)-THA[2] | 14 BNZ | 3.2 THP |
| monkey | 0.04 bis(7) THA[2] | 14 BNZ | 3.2 THP | 1.0 DZP[3] |
| monkey | 0.04 bis(7)-THA[2] | 15 CRM | |
| monkey | 0.04 bis(7)-THA[2] | 15 CRM | 1.0 DZP[3] |
| monkey | 0.04 bis(7)-THA[2] | 1.5 SCO | |
| monkey | 0.04 bis(7)-THA[2] | 1.5 SCO | 1.0 DZP[3] |

[1](−)-Hup-A is (−)-huperzine A. In the above examples 0.4 mg/kg (±)-huperzine A, 2.0 mg/kg (−)-huperzine B, 4.0 mg/kg (±)-huperzine B, 0.25 mg/kg (−)-10,10-dimethyl huperzine A, 0.5 mg/kg (±)-10,10-dimethyl huperzine A, 0.2 mg/kg (−)-HUPFD-13, or 0.4 mg/kg (±)-HUPFD-13 can be substituted for (−)-huperzine A.
[2]bis(7)-THA is bis(7)-tacrine. In the above examples 20 mg/kg tacrine, 4 mg/kg (−)-galanthamine, 2 mg/kg rivastigmine or 2 mg/kg donepezil can be substituted for bis(7)-tacrine.
[3]1.0 mg/kg MDZ can be substituted for DZP.

TABLE 5

| Subject | Dose of Active Ingredients (mg/kg) | | |
|---|---|---|---|
| human | 0.02 (−)-Hup-A[1] | 0.06 ATR | |
| human | 0.02 (−)-Hup-A[1] | 0.06 ATR | 0.1 DZP[3] |
| human | 0.02 (−)-Hup-A[1] | 0.3 BNZ | 0.06 THP |
| human | 0.02 (−)-Hup-A[1] | 0.3 BNZ | 0.06 THP | 0.1 DZP[3] |

TABLE 5-continued

| Subject | Dose of Active Ingredients (mg/kg) | | |
|---------|------|------|------|
| human | 0.02 (−)-Hup-A[1] | 0.4 CRM | |
| human | 0.02 (−)-Hup-A[1] | 0.4 CRM | 0.1 DZP[3] |
| human | 0.02 (−)-Hup-A[1] | 0.03 SCO | |
| human | 0.02 (−)-Hup-A[1] | 0.03 SCO | 0.1 DZP[3] |
| human | 0.004 bis(7)-THA[2] | 0.06 ATR | |
| human | 0.004 bis(7)-THA[2] | 0.06 ATR | 0.1 DZP[3] |
| human | 0.004 bis(7)-THA[2] | 0.3 BNZ | 0.06 THP |
| human | 0.004 bis(7) THA[2] | 0.3 BNZ | 0.06 THP | 0.1 DZP[3] |
| human | 0.004 bis(7)-THA[2] | 0.4 CRM | |
| human | 0.004 bis(7)-THA[2] | 0.4 CRM | 0.1 DZP[3] |
| human | 0.004 bis(7)-THA[2] | 0.03 SCO | |
| human | 0.004 bis(7)-THA[2] | 0.03 SCO | 0.1 DZP[3] |

[1](−)-Hup-A is (−)-huperzine A. In the above examples 0.04 mg/kg (±)-huperzine A, 0.2 mg/kg (−)-huperzine B, 0.4 mg/kg (±)-huperzine B, 0.025 mg/kg (−)-10,10-dimethyl huperzine A, 0.05 mg/kg (±)-10,10-dimethyl huperzine A, 0.02 mg/kg (−)-HUPFD-13, or 0.04 mg/kg (±)-HUPFD-13 can be substituted for (−)-huperzine A.
[2]bis(7)-THA is bis(7)-tacrine. In the above examples 2 mg/kg tacrine, 0.4 mg/kg (−)-galanthamine, 0.2 mg/kg rivastigmine or 0.2 mg/kg donepezil can be substituted for bis(7)-tacrine.
[3]0.1 mg/kg MDZ can be substituted for DZP.

Example 2

Table 6 shows examples of combinations of active ingredients that may used in humans for the prevention, treatment and/or reversal of the neurological diseases and disorders described in Table 2 beginning on page 22. Table 7 describes the combinations of active ingredients referenced in Table 6.

TABLE 6

| Description of Disease or Disorder[1] | Treatment Effect or Treatment Effect Evident on:[1] | Active Ingredient Combination Number[2] | Preferred Treatment Regimens[3] |
|---|---|---|---|
| age-associated cognitive decline | neuroprotection memory cognition | 1 | a, c, d |
| age-associated memory impairment | neuroprotection memory | 1 | a, c, d |
| AIDS dementia | neuroprotection memory mental concentration | 1, 4, 5, 6, 7, 12, 13, 14, 15 | a, c, d |
| alcoholism | neuroprotection craving withdrawal - seizures | 1, 4, 5, 6, 7, 12, 13, 14, 15 | a, c, d |
| Alzheimer's disease | neuroprotection memory cognition behavior | 1, 4, 5, 6, 7, 12, 13, 14, 15 | a, c, d |
| amyotrophic lateral sclerosis | neuroprotection muscle strength muscle atrophy | 1, 4, 5, 6, 7 | a, c, d |
| anxiety | anxiety symptoms | 1, 4, 5, 6, 7, 12, 13, 14, 15 | a, c, d |
| anxiety disorders | anxiety disorder symptoms | 1, 4, 5, 6, 7, 12, 13, 14, 15 | a, c, d |
| attention deficit disorder | cognition attention | 1 | a, c, d |
| attention deficit hyperactivity disorder | cognition attention hyperactivity | 1, 6, 14 | a, c, d |
| CNS incapacitating agents | cognition delusions | 1 | a, h |
| cocaine addiction | craving withdrawal | 1, 4, 6, 12, 14 | a, c, d |
| Creutzfeld-Jacob disease | neuroprotection memory muscle strength | 1, 4, 5, 6, 7, 12, 13, 14, 15 | a, c, d |
| depression | depression | 1, 4, 6, 12, 14 | a, c, d |
| Down syndrome | neuroprotection cognition language skills | 1 | a, c, d |
| eating disorders | compulsive behavior craving | 1, 4, 5, 6, 7, 12, 13, 14, 15 | a, c, d |
| epilepsy | neuroprotection seizures memory | 1, 4, 5, 6, 7, 12, 13, 14, 15 | a, c, d a, f (following seizure) |
| glaucoma | neuroprotection vision intraocular pressure | 1, 4, 5, 6, 7, 12, 13, 14, 15 | e |
| headache - migraine | pain | 1, 4, 6, 12, 14 | a, c, d |
| hepatic encephalopathy | neuroprotection memory mental concentration attention | 1, 4, 5, 6, 7, 12, 13, 14, 15 | a, c, d |

TABLE 6-continued

| Description of Disease or Disorder[1] | Treatment Effect or Treatment Effect Evident on:[1] | Active Ingredient Combination Number[2] | Preferred Treatment Regimens[3] |
|---|---|---|---|
| Huntington's disease | neuroprotection memory cognition | 1, 4, 5, 6, 7, 12, 13, 14, 15 | a, c, d |
| hyperalgesia | pain | 1, 4, 5, 6, 7, 12, 13, 14, 15 | a, c, d |
| hypoxic-ischemic encephalopathy | neuroprotection memory cognition seizures | 1, 4, 5, 6, 7, 12, 13, 14, 15 | a, f b, f (perinatal asphyxia) |
| Lewy body dementia | neuroprotection memory cognition | 1, 4, 5, 6, 7, 12, 13, 14, 15 | a, c, d |
| memory and cognitive improvement in healthy individuals | neuroprotection memory cognition | 1 | a, c, d |
| mild cognitive impairment | neuroprotection memory cognition | 1, 4, 5, 6, 7, 12, 13, 14, 15 | a, c, d |
| multiple sclerosis | neuroprotection memory attention mental concentration muscle strength | 1, 4, 5, 6, 7, 12, 13, 14, 15 | a, c, d |
| myasthenia gravis | muscle strength | 1, 2, 4, 6, 8 | a, c, d |
| neurogenic orthostatic hypotension | blood pressure | 1, 2, 4, 6, 8, 10, 12, 14, 16 | a, c, d |
| neurologic complications of cardiac surgery | neuroprotection memory | 1, 4, 5, 6, 7, 12, 13, 14, 15 | a, f, g |
| neuromuscular block | muscle function | 1 | b |
| nicotine addiction | craving | 1, 4, 6, 12, 14 | a, c, d |
| obsessive compulsive disorder | craving | 1, 4, 5, 6, 7, 12, 13, 14, 15 | a, c, d |
| olivopontocerebellar atrophy | neuroprotection memory cognition muscle strength | 1, 4, 5, 6, 7, 12, 13, 14, 15 | a, c, d |
| opiate addiction | craving | 1, 4, 5, 6, 7, 12, 13, 14, 15 | a, c, d |
| pain - acute | pain | 1, 4, 5, 6, 7, 12, 13, 14, 15 | a, c, d |
| pain - chronic | pain | 1, 4, 5, 6, 7, 12, 13, 14, 15 | a, c, d |
| Parkinson's disease | neuroprotection memory cognition | 1, 4, 5, 6, 7, 12, 13, 14, 15 | a, c, d |
| peripheral nerve injury | | 1, 4, 5, 6, 7, 12, 13, 14, 15 | a, f |
| post-polio syndrome | neuroprotection muscle strength | 1, 2, 4, 6, 8 | a, c, d |
| psychomotor skill improvement in healthy individuals | performance of complex tasks | 1 | a, c, d |
| retinal diseases | neuroprotection vision | 1, 4, 5, 6, 7, 12, 13, 14, 15 | a, c, d, e |
| Rett syndrome | neuroprotection cognition muscle strength seizures | 1, 4, 5, 6, 7, 12, 13, 14, 15 | a, c, d |
| schizophrenia | memory cognition | 1 | a, c, d |
| seizure disorders | neuroprotection seizures convulsions | 1, 4, 5, 6, 7, 12, 13, 14, 15 | a, c, d a, f (following seizure) |
| spasticity | dystonic movement | 1, 4, 5, 6, 7, 12, 13, 14, 15 | a, c, d |
| spinal cord injury | neuroprotection muscle strength | 1, 4, 5, 6, 7, 12, 13, 14, 15 | a, f |
| stroke - acute | neuroprotection memory | 1, 4, 5, 6, 7, 12, 13, 14, 15 | a, f |
| tardive dyskinesia | neuroprotection dystonic movement | 1, 4, 5, 6, 7, 12, 13, 14, 15 | a, c, d |
| tinnitus | neuroprotection hearing | 1, 4, 5, 6, 7, 12, 13, 14, 15 | a, c, d |
| transient ischemic attack | neuroprotection | 1, 4, 5, 6, 7, 12, 13, 14, 15 | a, c, d |

TABLE 6-continued

| Description of Disease or Disorder[1] | Treatment Effect or Treatment Effect Evident on:[1] | Active Ingredient Combination Number[2] | Preferred Treatment Regimens[3] |
|---|---|---|---|
| traumatic brain injury | neuroprotection memory cognition | 1, 4, 5, 6, 7, 12, 13, 14, 15 | a, f |
| vascular dementia | neuroprotection memory cognition | 1, 4, 5, 6, 7, 12, 13, 14, 15 | a, c, d |
| Wernicke-Korsakoff syndrome | memory cognition | 1 | a, c, d |

[1]See Table 2 beginning on page 22 for further information.
[2]See Table 7 on page 41 for description of active ingredient combinations.
[3]Preferred treatment regimens.
a. Oral administration is preferred. If oral administration not feasible or not medically indicated, then administer by intramuscular injection with dose adjusted as necessary by physician.
b. Intramuscular administration. Dose adjusted as necessary by physician.
c. Preferably administer 2 times per day. May be administered 3 times per day with appropriate adjustment to dosage.
d. Optimal dose will vary from one individual to another. For best treatment effect and to minimize side effects it is preferred that dosing is started at 20% of stated dose. Subject should remain at said dose for approximately 2-4 weeks, then increase the dose to 40% of the stated dose. This escalation regimen is repeated until reaching dose that produces optimal symptomatic improvement, 100% of stated dose, or as otherwise recommended by healthcare professional.
e. Topical administration as directed by healthcare professional.
f. Start with maximum tolerated initial dose. Continue maximum tolerated b.i.d. dose during acute phase. Following acute phase continue b.i.d. with dose providing best symptomatic improvement.
g. Start initial dose approximately 1 hour before surgery.
h. Double initial dosage if anticholinergic symptoms are evident. Repeat administration at 90 minute intervals until anticholinergic symptoms subside.

TABLE 7

| Combination Number | Dose of Active Ingredients (μg/kg) | | | |
|---|---|---|---|---|
| 1 | 7.5 (−)-Hup-A[1] | | | |
| 2 | 7.5 (−)-Hup-A[1] | 15 ATR | | |
| 3 | 7.5 (−)-Hup-A[1] | 15 ATR | 70 DZP[3] | |
| 4 | 7.5 (−)-Hup-A[1] | 150 BNZ | 30 THP | |
| 5 | 7.5 (−)-Hup-A[1] | 150 BNZ | 30 THP | 70 DZP[3] |
| 6 | 7.5 (−)-Hup-A[1] | 200 CRM | | |
| 7 | 7.5 (−)-Hup-A[1] | 200 CRM | 70 DZP[3] | |
| 8 | 7.5 (−)-Hup-A[1] | 10 SCO | | |
| 9 | 7.5 (−)-Hup-A[1] | 10 SCO | 70 DZP[3] | |
| 10 | 1.5 bis(7)-THA[2] | 15 ATR | | |
| 11 | 1.5 bis(7)-THA[2] | 15 ATR | 70 DZP[3] | |
| 12 | 1.5 bis(7)-THA[2] | 150 BNZ | 30 THP | |
| 13 | 1.5 bis(7) THA[2] | 150 BNZ | 30 THP | 70 DZP[3] |
| 14 | 1.5 bis(7)-THA[2] | 200 CRM | | |
| 15 | 1.5 bis(7)-THA[2] | 200 CRM | 70 DZP[3] | |
| 16 | 1.5 bis(7)-THA[2] | 10 SCO | | |
| 17 | 1.5 bis(7)-THA[2] | 10 SCO | 70 DZP[3] | |

[1](−)-Hup-A is (−)-huperzine A. In the above examples 15 μg/kg (±)-huperzine A, 300 μg (+)-huperzine A, 75 μg/kg (−)-huperzine B, 150 μg/kg (±)-huperzine B, 9.5 μg/kg (−)-10,10-dimethyl huperzine A, 19 μg/kg (±)-10,10-dimethyl huperzine A, 7.5 μg/kg (−)-HUPFD-13, 15 μg/kg (±)-HUPFD-13, or 300 μg (+)-HUPFD-13 can be substituted for (−)-huperzine A.
[2]bis(7)-THA is bis(7)-tacrine. In the above examples 750 μg/kg tacrine, 150 μg/kg (−)-galanthamine, 75 μg/kg rivastigmine or 75 μg/kg donepezil can be substituted for bis(7)-tacrine.
[3]70 μg/kg MDZ can be substituted for DZP.

REFERENCES

1. Ashani Y, Grunwald J, Akalai D, et al. Studies with Huperzine A, a New Candidate in the Research of Prophylaxis against Nerve Agents. In: *Proceedings of the 1996 Medical Defense Bioscience Review.* p. 105-110 (1996).
2. Berry W K, Davies D R. The Use of Carbamates and Atropine in the Protection of Animals Against Poisoning by 1,2,2-Trimethylpropyl-methylphosphonofluoridate. *Biochemical Pharmacology.* 19(3):927-934 (1970).
3. Cheng S H and X C Tang. Comparative Studies of Huperzine A, E2020, and Tacrine on Behavior and Cholinesterase Activities. *Pharmacology Biochemistry and Behavior.* 60(2):377-386 (1998).
4. Grunwald J, Raveh L, Doctor B P, et al. Huperzine A as a Pretreatment Candidate Drug against Nerve Agent Toxicity. *Life Sciences* 54(13):991-997 (1994).
5. Kassa J, Vachek J, Bajgar J, et al. A Combination of Pyridostigmine with Anticholinergic Drugs Effective Pharmacological Pretreatment of Soman-Poisoned Mice. *The ASA Newsletter. Article* 00-6A. accessed on the Internet (2001).
6. Krejcova G, Kassa J. Neuroprotective efficacy of pharmacological pretreatment and antidotal treatment in tabun-poisoned rats. *Toxicology* 185:129-139 (2003).
7. Lallement G, Foquin A, Dorandeu F, et al. Subchronic Administration of Various Pretreatments of Nerve Agent Poisoning. II. Compared Efficacy Against Soman Toxicity. *Drug and Chemical Toxicity.* 24(2): 165-180 (2001a).
8. Lallement G, Veyret J, Masqueliez M, Aubriot S, Burckhart M F, Baubichon D. Efficacy of huperzine in preventing soman-induced seizures neuropathological changes and lethality. *Fund Clin Pharmacol.* 11:387-94 (1997).
9. Qian H C, Wang M, Zhou Z F, et al. Pharmacokinetics of tablet huperzine A in six volunteers. *Acta Pharmacologica Sinica* 16(5):396-398 (1995).
10. Raveh L, Chapman S, Cohen G, et al. The involvement of the NMDA receptor complex in the protective effect of anticholinergic drugs against soman poisoning. *NeuroToxicology* 20:535-49 (1999).
11. Raveh L, Weissman B A, Cohen G, et al. Caramiphen and Scopolamine Prevent Soman-Induced Brian Damage and Cognitive Dysfunction. *NeuroToxicology* 23: 7-17 (2002).
12. Shang Y Z, Ye J W, Tang X C, et al. Improving effects of huperzine A on abnormal lipid peroxidation and superoxide dismutase in aged rats. *Acta Pharmacol Sin.* 20(9):824-828 (1999).
13. Sommer A, Bleyer H. Nerve gas antidote. U.S. Pat. No. 5,298,504 (1994).
14. Tang, X C, De Sarno P, Sugaya K, et al. Effect of huperzine A, a new cholinesterase inhibitor, on the central cholinergic system of the rat. *J Neurosci Res.* 24(2):276-285 (1989).

15. Tonduli L S, Testylier G, Masqueliez C, et al. Effects of Huperzine Used as Pre-Treatment Against Soman-Induced Seizures. *NeuroToxicology* 22:29-37 (2001).
16. Ved H S, Koenig M K, Dave J R, et al. Huperzine A, a potential therapeutic agent for dementia, reduces neuronal cell death caused by glutamate. *NeuroReport.* 8:963-968 (1997).
17. Ved, H S, Nguyen T, Hale S, et al. Huperzine A Reduces Organophosphate and NMDA Induced Seizures. *Proceedings of the 2000 Medical Defense Bioscience Review*, Baltimore Md. (2000a).
18. Wang Y E, Feng J, Lu W H, et al. Pharmacokinetics of Huperzine A in Rats and Mice. *Acta Pharmacol Sin.* 9(3): 193-196 (1988).
19. Wang L M, Han Y F, Tang X C. Huperzine A improves cognitive deficits caused by chronic cerebral hypoperfusion in rats. *Brain Research.* 398:65-72 (2000).
20. Wang L S, Zhou J, Shao X M, et al. Huperzine A attenuated cognitive deficits and brain injury in neonatal rats after hypoxia-ischemia. *Brain Research.* 949:162-170 (2002).
21. Wang R, Zhang H Y, Tang X C. Huperzine A attenuates cognitive dysfunction and neuronal degeneration caused by β-amyloid protein-(140) in rat. *European Journal of Pharmacology.* 421:149-156 (2001).
22. Zhang H Y, Liang Y Q, Tang X C, et al. Stereoselectivities of enantiomers of huperzine A in protection against β-amyloid$_{25-35}$-induced injury in PC12 and NG108-15 cells and cholinesterase inhibition in mice. *Neuroscience Letters.* 317:143-146 (2002).
23. Zhang Y H, Chen X Q, Yang H H, et al. Similar potency of the enantiomers of huperzine A in inhibition of [$^3$H]dizocilpine [MK-801] binding in rat cerebral cortex. *Neuroscience Letters* 295:116-118 (2000).

What is claimed is:

1. A method for reducing or delaying symptoms or reducing mortality associated with poisoning of a mammalian subject by an organophosphate nerve agent or by an organophosphate insecticide comprising pretreating the mammalian subject in need thereof with (a) 1.25 to 5000 μg/kg/day of a huperzine compound or pharmaceutically acceptable salt or hydrate thereof, and (b) 0.05 to 100 mg/kg/day caramiphen or pharmaceutically acceptable salt or hydrate thereof.

2. The method of claim 1, wherein the poisoning is by an organophosphate nerve agent and the agent is cyclosarin, sarin, soman, tabun, VR, VX, Novichok-5 or Novichok-7, and the organophosphate insecticide is azinphos-methyl, bomyl, dimefos, methamidophos, or methyl parathion.

3. The method of claim 1, wherein the poisoning is by an organophosphate nerve agent and the agent is soman.

4. The method of claim 1, wherein the huperzine compound is (−)-huperzine A, (+)-huperzine A, (±)-huperzine A, (−)-huperzine B, (+)-huperzine B, or (±)-huperzine B; (+)-10-methyl huperzine A, (−)-10-methyl huperzine A, (±)-10-methyl huperzine A, (+)-10,10-dimethyl huperzine A, (−)-10,10-dimethyl huperzine A, (±)-10,10-dimethyl huperzine A; N,N'-di-5'-(5',6',7',8'-tetrahydroquinolin-2-onyl)-1,12-diaminododecane; N,N'-di-5'-(5',6',7',8'-tetrahydroquinolin-2-onyl)-1,13-diaminotridecane; or N,N'-di-5'-(5',6',7',8'-tetrahydroquinolin-2-onyl)-1,14-diaminotetradecane as the (+), (−), and (±) forms thereof.

5. The method of claim 4, wherein the huperzine compound is (+)-huperzine A.

6. The method of claim 4, wherein the huperzine compound is (−)-huperzine A.

* * * * *

UNITED STATES PATENT AND TRADEMARK OFFICE
CERTIFICATE OF CORRECTION

| | | |
|---|---|---|
| PATENT NO. | : 8,299,062 B2 | Page 1 of 1 |
| APPLICATION NO. | : 10/943502 | |
| DATED | : October 30, 2012 | |
| INVENTOR(S) | : Frankin Volvovitz | |

It is certified that error appears in the above-identified patent and that said Letters Patent is hereby corrected as shown below:

Title Page, item (60) and in the specification, col. 1, lines 5-7 should read as follows:

This application claims the benefit of U.S. Provisional Application No. 60/504,361, filed Sep. 17, 2003, hereby incorporated herein by reference in its entirety.

Signed and Sealed this
Thirteenth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,299,062 B2 | Page 1 of 1 |
| APPLICATION NO. | : 10/943502 | |
| DATED | : October 30, 2012 | |
| INVENTOR(S) | : Volvovitz | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1405 days.

Signed and Sealed this
Second Day of September, 2014

Michelle K. Lee
*Deputy Director of the United States Patent and Trademark Office*